United States Patent
Son et al.

(10) Patent No.: US 12,246,002 B2
(45) Date of Patent: Mar. 11, 2025

(54) PHARMACEUTICAL COMPOSITION FOR PREVENTION OR TREATMENT OF CIRCADIAN RHYTHM-RELATED DISORDERS, COMPRISING OXYIMINOMETHYLBENZENE DERIVATIVE AS ACTIVE INGREDIENT

(71) Applicants: KOREA UNIVERSITY RESEARCH AND BUSINESS FOUNDATION, Seoul (KR); KYUNGPOOK NATIONAL UNIVERSITY INDUSTRY-ACADEMIC COOPERATION FOUNDATION, Daegu (KR)

(72) Inventors: Gi Hoon Son, Seoul (KR); Jong Hwa Jung, Daegu (KR)

(73) Assignees: KOREA UNIVERSITY RESEARCH AND BUSINESS FOUNDATION, Seoul (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 852 days.

(21) Appl. No.: 17/413,406

(22) PCT Filed: Sep. 27, 2019

(86) PCT No.: PCT/KR2019/012565
§ 371 (c)(1),
(2) Date: Jun. 11, 2021

(87) PCT Pub. No.: WO2020/122380
PCT Pub. Date: Jun. 18, 2020

(65) Prior Publication Data
US 2022/0062215 A1    Mar. 3, 2022

(30) Foreign Application Priority Data

Dec. 13, 2018    (KR) .................. 10-2018-0160777

(51) Int. Cl.
*A61K 31/216* (2006.01)
*A61K 31/22* (2006.01)
(Continued)

(52) U.S. Cl.
CPC ............ *A61K 31/216* (2013.01); *A61K 31/22* (2013.01); *A61P 3/00* (2018.01); *A61P 3/04* (2018.01);
(Continued)

(58) Field of Classification Search
CPC .... A61K 31/216; A61K 31/195; A61K 31/22; A61P 3/04; A61P 25/30; A61P 3/00; A61P 25/00; A61P 35/00
See application file for complete search history.

(56) References Cited

FOREIGN PATENT DOCUMENTS

| KR | 20140017332 | 2/2014 |
|----|-------------|--------|
| KR | 101497577   | 3/2015 |

(Continued)

OTHER PUBLICATIONS

Machine translation for KR20140017332A. Google patents. Access Dec. 11, 2024. (Year: 2014).*

(Continued)

*Primary Examiner* — Clinton A Brooks
*Assistant Examiner* — Kyle Nottingham
(74) *Attorney, Agent, or Firm* — Hodgson Russ LLP

(57) ABSTRACT

The present disclosure relates to a pharmaceutical composition for prevention or treatment of circadian rhythm-related disorders, including an oxyiminomethylbenzene derivative or a pharmaceutically acceptable salt thereof.

10 Claims, 2 Drawing Sheets

(51) Int. Cl.
*A61P 3/00* (2006.01)
*A61P 3/04* (2006.01)
*A61P 25/00* (2006.01)
*A61P 25/30* (2006.01)
*A61P 35/00* (2006.01)

(52) U.S. Cl.
CPC ............... *A61P 25/00* (2018.01); *A61P 25/30* (2018.01); *A61P 35/00* (2018.01)

(56) References Cited

FOREIGN PATENT DOCUMENTS

| KR | 20170042438 | 4/2017 |
| KR | 101885052 | 8/2018 |
| WO | 2008035359 | 3/2008 |
| WO | 2008124878 | 10/2008 |
| WO | 2014192023 | 12/2014 |
| WO | 2015107541 | 7/2015 |

OTHER PUBLICATIONS

Machine translation for KR20170042438A. Google patents. Access Dec. 11, 2024. (Year: 2017).*
Bur et al., "The circadian clock components CRY1 and CRY2 are necessary to sustain sex dimorphism in mouse liver metabolism," The Journal of Biological Chemistry, 2009, vol. 284, No. 14, pp. 9066-9073.
Chen et al., "Development and Therapeutic Potential of Small-Molecule Modulators of Circadian Systems," Annual Review of Pharmacology and Toxicology, 2018, vol. 58, pp. 231-252.
Chun et al., "Identification and validation of cryptochrome inhibitors that modulate the molecular circadian clock," ACS Chemical Biology, 2014, vol. 9, pp. 703-710.
Chun et al., "A synthetic cryptochrome inhibitor induces antiproliferative effects and increases chemosensitivity in human breast cancer cells," Biochemical and Biophysical Research Communications, 2015, vol. 467, pp. 441-446.
Chung et al., "Impact of circadian nuclear receptor REV-ERBα on midbrain dopamine production and mood regulation," Cell, 2014, vol. 157, pp. 858-868.
Gouin et al., "Altered expression of circadian rhythm genes among individuals with a history of depression," Journal of Affective Disorders, 2010, vol. 126, Nos. 1-2, pp. 161-166.
Jang et al., "The cryptochrome inhibitor KS15 enhances E-box-mediated transcription by disrupting the feedback action of a circadian transcription-repressor complex," Life Sciences, 2018, vol. 200, pp. 49-55.
Hood et al., "Neurodegeneration and the Circadian Clock," Frontiers in Aging Neuroscience, 2017, vol. 9, No. 170, 9 pages.
Lamia et al., "Physiological significance of a peripheral tissue circadian clock," Proceedings of the National Academy of Sciences of the United States of America, 2018, vol. 105, No. 39, pp. 15172-15177.
Gorbacheva et al., "Circadian sensitivity to the chemotherapeutic agent cyclophosphamide depends on the functional status of the CLOCK/BMAL1 transactivation complex," Proceedings of the National Academy of Sciences of the United States of America, 2005, vol. 102, No. 9, pp. 3407-3412.
Kojetin, "REV-ERB and ROR nuclear receptors as drug targets," Nature Reviews Drug Discovery, 2014, vol. 13, No. 3, pp. 197-216.
Lauretti et al., "Circadian rhythm dysfunction: a novel environmental risk factor for Parkinson's disease," Molecular Psychiatry, 2017, vol. 22, pp. 280-286.
Lee et al., "Development of Small-Molecule Cryptochrome Stabilizer Derivatives as Modulators of the Circadian Clock," ChemMedChem, 2015, vol. 10, pp. 1489-1497.
Mcclung et al., "Regulation of dopaminergic transmission and cocaine reward by the Clock gene," Proceedings of the National Academy of Sciences of the United States of America, 2005, vol. 102, No. 26, pp. 9377-9381.

Menculini et al., "Depressive mood and circadian rhythms disturbances as outcomes of seasonal affective disorder treatment: A systematic review," Journal of Affective Disorders, 2018, vol. 241, pp. 608-626.
Moon et al., "Advanced Circadian Phase in Mania and Delayed Circadian Phase in Mixed Mania and Depression Returned to Normal after Treatment of Bipolar Disorder," EBioMedicine, 2016, vol. 11, pp. 285-295.
Musiek et al., "Circadian clock proteins regulate neuronal redox homeostasis and neurodegeneration," The Journal of Clinical Investigation, 2013, vol. 123, No. 12, pp. 5389-5400.
Ozturk et al., "Loss of cryptochrome reduces cancer risk in p53 mutant mice," Proceedings of the National Academy of Sciences of the United States of America, 2009, vol. 106, No. 8, pp. 2841-2846.
Rudic et al., "BMAL1 and Clock, two essential components of the circadian clock, are involved in glucose homeostasis," PLOS Biology, 2004, vol. 2, No. 11: e377, pp. 1893-1899.
Scheer et al., "Adverse metabolic and cardiovascular consequences of circadian misalignment," Proceedings of the National Academy of Sciences of the United States of America, 2009, vol. 106, No. 11, pp. 4453-4458.
Schernhammer et al., "Rotating night shifts and risk of breast cancer in women participating in the nurses' health study," Journal of the National Cancer Institute, 2001, vol. 93, No. 20, pp. 1563-1568.
Schirmacher et al., "Sequence variants in circadian rhythmic genes in a cohort of patients suffering from hypersomnia of central origin," Biological Rhythm Research, 2011, vol. 42, No. 5, pp. 407-416.
Schnell et al., "Mice lacking circadian clock components display different mood-related behaviors and do not respond uniformly to chronic lithium treatment," Chronobiology International: The Journal of Biological and Medical Rhythm Research, 2015, vol. 32, No. 8, pp. 1075-1089.
Shimba et al., "Brain and muscle Arnt-like protein-1 (BMAL1), a component of the molecular clock, regulates adipogenesis," Proceedings of the National Academy of Sciences of the United States of America, 2005, vol. 102, No. 34, pp. 12071-12076.
Son et al., "Adrenal peripheral clock controls the autonomous circadian rhythm of glucocorticoid by causing rhythmic steroid production," Proceedings of the National Academy of Sciences of the United States of America, 2008, vol. 105, No. 52, pp. 20970-20975.
Spiegel et al., "Effects of poor and short sleep on glucose metabolism and obesity risk," Nature Reviews Endocrinology, 2009, vol. 5, No. 5, pp. 253-261.
Stratmann et al., "Properties, entrainment, and physiological functions of mammalian peripheral oscillators," Journal of Biological Rhythms, 2006, vol. 21, No. 6, pp. 494-506.
Traschel et al., "Sleep homeostasis in suprachiasmatic nuclei-lesioned rats: effects of sleep deprivation and triazolam administration," Brain Research, 1992, vol. 589, pp. 253-261.
Turek et al., "Obesity and metabolic syndrome in circadian Clock mutant mice," Science, 2005, vol. 308, No. 5724, pp. 1043-1045.
Van Der Horst et al., "Mammalian Cry1 and Cry2 are essential for maintenance of circadian rhythms," Nature, 1999, vol. 398, pp. 627-630.
Wisor et al., "A role for cryptochromes in sleep regulation," BMC Neuroscience, 2002, vol. 3, No. 20, 14 pages.
Yoo et al., "PERIOD2::LUCIFERASE real-time reporting of circadian dynamics reveals persistent circadian oscillations in mouse peripheral tissues," Proceedings of the National Academy of Sciences of the United States of America, 2004, vol. 101, No. 15, pp. 5339-5346.
Zhang et al., "Cryptochrome mediates circadian regulation of cAMP signaling and hepatic gluconeogenesis," Nature Medicine, 2010, vol. 16, No. 10, pp. 1152-1156.
PubChem Database, PubChem Compound, retrieved from the internet, 2020, 5 pages.
WIPO, International Search Report for PCT/KR2019/012565, Jan. 2, 2020.

* cited by examiner

PHARMACEUTICAL COMPOSITION FOR PREVENTION OR TREATMENT OF CIRCADIAN RHYTHM-RELATED DISORDERS, COMPRISING OXYIMINOMETHYLBENZENE DERIVATIVE AS ACTIVE INGREDIENT

CROSS-REFERENCE TO RELATED APPLICATIONS

The present application is a national phase entry under 35 U.S.C. § 371 of international application PCT/KR2019/012565, filed on Sep. 27, 2019, which claims priority to KR application No. 10-2018-0160777, filed on Dec. 13, 2018. The entire disclosures of the above-referenced applications are incorporated by reference herein.

TECHNICAL FIELD

The present disclosure relates to a pharmaceutical composition for preventing or treating circadian rhythm-related diseases, including an oxyiminomethylbenzene derivative or a pharmaceutically acceptable salt thereof as an active ingredient.

BACKGROUND ART

Like all living things on the Earth, humans also exhibit a circadian rhythm that is tailored to the 24-hour period according to the change of day and night in terms of physiological or behavioral aspects. The most well-known human circadian rhythm behavior is sleep, but in addition to this, body temperature, diet, hormones, blood sugar levels and other metabolic activities in the body, and the cell division period are also regulated by this circadian rhythm. Disruption of the intrinsic circadian rhythm due to genetic or environmental causes may lead to various pathological conditions referred to as circadian rhythm-related disorders. In particular, in the industrialized modern society, most people are exposed to various environmental causes of circadian clock disturbances, such as excessive night lighting, excessive night activities such as shift work, and abnormal diet patterns. For this reason, research on the cause and treatment of circadian rhythm-related disease is increasing in importance.

Organisms have genes for the control of circadian rhythm. The circadian rhythm control gene regulates circadian rhythm. Recent research has identified a network of biological clock molecules that govern the circadian rhythm. Mammalian circadian rhythm control genes include Period (PER) genes (Per1, Per2, Per3), CLOCK gene, BMAL genes (Bmal1, Bmal2), Cryptochrome (CRY) genes (Cry1, Cry2), REV-ERB genes (Rev-erbα, Rev-erbβ), ROR genes (Rora, Rorb, Rorc), etc. They form a molecular clock network. In particular, at the highest level, the heterodimer of CLOCK and BMAL1 protein acts as a transcription factor and binds to the cis-element E-box present in the promoter of the PER and CRY genes which are feedback genes located at the lower level, thereby triggering its expression. A series of molecular circulatory structures in which the gene products inhibit their upstream transcription factors are the core of the circadian rhythm molecular biological clock, and is called the biological clock core loop. These molecular networks are known to affect various physiological processes by triggering the circadian rhythm of sub-regulated genes (non-patent document 1). In addition, molecular networks of these circadian rhythm biological clock genes have been found in various peripheral organs as well as in the suprachiasmatic nucleus (SCN) of the hypothalamus where the central biological clock of mammals is located. Also in cells of these peripheral organs, the biological clock molecular network is also periodically expressed at an independent circadian rhythm in a pattern similar to that of the suprachiasmatic nucleus (SCN). The biological clock molecular network expressed in these various peripheral organs is called a peripheral or local clock in contrast to the central biological clock (non-patent document 1).

Since the biological clock is a general-purpose control device that regulates overall behavior and physiology, the types of circadian rhythm-related diseases are extensive and include sleep disorders, shift-work fatigue, cancer, metabolic diseases, cardiovascular diseases, immune and inflammatory diseases, mood disorders, addiction disorders, and neurodegenerative diseases.

In fact, it was reported that emergency workers who work in shifts while changing the normal 24-hour rhythm of wake up and sleep are at risk of developing various diseases including metabolic disorders such as diabetes (non-patent document 2). It has been reported through an epidemiologic study of nurses exposed to long-term shift work, that the number and intensity of their shift work causes a higher breast cancer rate than that of normal people (non-patent document 3).

There have been many studies on the cause and treatment of circadian rhythm-related diseases due to various environmental and genetic circadian clock disturbances. One of them is to regulate the circadian rhythm through phosphorylation of key genes of the circadian clock. After it was known that mammalian kinases, casein kinase Iε (CKIε) and casein kinase Iδ (CKIδ) regulate the circadian rhythm by phosphorylating the key genes of the biological clock, researches have been conducted to regulate the circadian rhythm by targeting the CM protein (non-patent document 4). However, suppressing the CM gene does not directly affect the biological clock molecular network, so its effect is insignificant.

Another study is a study on Rev-erbα/β, a gene that constitutes the biological clock auxiliary loop. This is to adjust the circadian rhythm through an agonist and antagonist for REV-ERBα/β that inhibits the expression of BMAL1 (non-patent document 5). The main role of REV-ERBα/β is to slow the activity of the CLOCK:BMAL1 dimer in the molecular network of biological clocks, thereby performing fine-tuning necessary for the clock to function properly. However, this may not effectively adjust the circadian rhythm.

Recently, it was found that KS15 as a kind of 2-ethoxypropionic acid derivatives increase the transcriptional activity of CLOCK:BMAL1 heterodimer through inhibition of CRY protein. However, KS15 disrupted circadian rhythmicity of molecular clock by constitutively overactivating the CLOCK:BMAL1 heterodimer (non-patent document 6).

Therefore, at the present time when the physiological and clinical importance of the circadian rhythm is highlighted, it is urgent to develop a drug that can enhance or reinforce the circadian rhythmicity of the cellular clockworks by acting on the core loop of the molecular circadian clock for the prevention and treatment of various circadian rhythm-related diseases.

(Non-patent document 1) Stratmann M, Schibler U. Properties, entrainment, and physiological functions of mammalian peripheral oscillators. J Biol Rhythms. (2006) 21(6): 494-506.

(Non-patent document 2) Scheer F A, Hilton M F, Mantzoros C S, Shea S A. Adverse metabolic and cardiovascular consequences of circadian misalignment. Proc Natl Acad Sci USA. (2009) 106(11): 4453-4458.

(Non-patent document 3) Schemhammer E S, Laden F, Speizer F E, Willett W C, Hunter D J, Kawachi I, Colditz G A. Rotating night shifts and risk of breast cancer in women participating in the nurses' health study. J Natl Cancer Inst. (2001) 93(20): 1563-1568.

(Non-patent document 4) Chen Z, Yoo S H, Takahashi J S. Development and Therapeutic Potential of Small-Molecule Modulators of Circadian Systems. Annu Rev Pharmacol Toxicol. (2018) 58: 231-252.

(Non-patent document 5) Kojetin D J, Burris T P. REV-ERB and ROR nuclear receptors as drug targets. Nat Rev Drug Discov. (2014) 13(3): 197-216.

(Non-patent document 6) Chun S K, Jang J, Chung S, Yun H, Kim N J, Jung J W, Son G H, Suh Y G, Kim K. Identification and validation of cryptochrome inhibitors that modulate the molecular circadian clock. ACS Chem Biol. (2014) 9(3): 703-710.

(Non-patent document 7) Son G H, Chung S, Choe H K, Kim H D, Baik S M, Lee H, Lee H W, Choi S, Sun W, Kim H, Cho S, Lee K H, Kim K. Adrenal peripheral clock controls the autonomous circadian rhythm of glucocorticoid by causing rhythmic steroid production. Proc Natl Acad Sci USA. (2008) 105(52): 20970-20975.

(Non-patent document 8) Schirmacher A, Hor H, Heidbreder A, Happe S, Kelsch R, Kuhlenbaumer G, Meiẞa (Non-patent document 9) Wisor J P, O'Hara B F, Terao A, Selby C P, Kilduff T S, Sancar A, Edgar D M, Franken P. A role for cryptochromes in sleep regulation. BMC Neurosci. (2002) 3: 20.

(Non-patent document 10) Trachsel L, Edgar D M, Seidel W F, Heller H C, Dement W C. Sleep homeostasis in suprachiasmatic nuclei-lesioned rats: effects of sleep deprivation and triazolam administration. Brain Res. (1992) 589(2): 253-261.

(Non-patent document 11) Spiegel K, Tasali E, Leproult R, Van Cauter E. Effects of poor and short sleep on glucose metabolism and obesity risk. Nat Rev Endocrinol. (2009) 5(5): 253-261.

(Non-patent document 12) Turek F W, Joshu C, Kohsaka A, Lin E, Ivanova G, McDearmon E, Laposky A, Losee-Olson S, Easton A, Jensen D R, Eckel R H, Takahashi J S, Bass J. Obesity and metabolic syndrome in circadian Clock mutant mice. Science. (2005) 308 (5724): 1043-1045.

(Non-patent document 13) Lamia K A, Storch K F, Weitz C J. Physiological significance of a peripheral tissue circadian clock. Proc Natl Acad Sci USA. (2008) 105(39): 15172-15177.

(Non-patent document 14) Rudic R D, McNamara P, Curtis A M, Boston R C, Panda S, Hogenesch J B, Fitzgerald G A. BMAL1 and CLOCK, two essential components of the circadian clock, are involved in glucose homeostasis. PLoS Biol. (2004) 2(11): e377.

(Non-patent document 15) Shimba S, Ishii N, Ohta Y, Ohno T, Watabe Y, Hayashi M, Wada T, Aoyagi T, Tezuka M. Brain and muscle Arnt-like protein-1 (BMAL1), a component of the molecular clock, regulates adipogenesis. Proc Natl Acad Sci USA. (2005) 102(34):12071-12076.

(Non-patent document 16) Bur I M, Cohen-Solal A M, Carmignac D, Abecassis P Y, Chauvet N, Martin A O, van der Horst G T, Robinson I C, Maurel P, Mollard P, Bonnefont X. The circadian clock components CRY1 and CRY2 are necessary to sustain sex dimorphism in mouse liver metabolism. J Biol Chem. (2009) 284(14): 9066-9073.

(Non-patent document 17) Zhang E E, Liu Y, Dentin R, Pongsawakul P Y, Liu A C, Hirota T, Nusinow D A, Sun X, Landais S, Kodama Y, Brenner D A, Montminy M, Kay S A. Cryptochrome mediates circadian regulation of cAMP signaling and hepatic gluconeogenesis. Nat Med. (2010) 16(10):1152-1156.

(Non-patent document 18) Gouin J P, Connors J, Kiecolt-Glaser J K, Glaser R, Malarkey W B, Atkinson C, Beversdorf D, Quan N. Altered expression of circadian rhythm genes among individuals with a history of depression. J Affect Disord. (2010) 126(1-2): 161-166.

(Non-patent document 19) McClung C A, Sidiropoulou K, Vitaterna M, Takahashi J S, White F J, Cooper D C, Nestler E J. Regulation of dopaminergic transmission and cocaine reward by the Clock gene. Proc Natl Acad Sci USA. (2005) 102(26): 9377-9381.

(Non-patent document 20) Chung S, Lee E J, Yun S, Choe H K, Park S B, Son H J, Kim K S, Dluzen D E, Lee I, Hwang O, Son G H, Kim K. Impact of circadian nuclear receptor REV-ERBα on midbrain dopamine production and mood regulation. Cell. (2014) 157(4): 858-868.

(Non-patent document 21) Schnell A, Sandrelli F, Ranc V, Ripperger J A, Brai E, Albert L, Rainer G, Albrecht U. Mice lacking circadian clock components display different mood-related behaviors and do not respond uniformly to chronic lithium treatment. Chronobiol Int. (2015) 32(8): 1075-1089.

(Non-patent document 22) Moon J H, Cho C H, Son G H, Geum D, Chung S, Kim H, Kang S G, Park Y M, Yoon H K, Kim L, Jee H J, An H, Kripke D F, Lee H J. Advanced Circadian Phase in Mania and Delayed Circadian Phase in Mixed Mania and Depression Returned to Normal after Treatment of Bipolar Disorder. EBioMedicine. (2016) 11:285-295.

(Non-patent document 23) Menculini G, Verdolini N, Murru A, Pacchiarotti I, Volpe U, Cervino A, Steardo L, Moretti P, Vieta E, Tortorella A. Depressive mood and circadian rhythms disturbances as outcomes of seasonal affective disorder treatment: A systematic review. J Affect Disord. (2018) 241: 608-626.

(Non-patent document 24) Hood S, Amir S. Neurodegeneration and the Circadian Clock. Front Aging Neurosci. (2017) 9: 170.

(Non-patent document 25) Musiek E S, Lim M M, Yang G, Bauer A Q, Qi L, Lee Y, Roh R I, Ortiz-Gonzalez X, Dearborn J T, Culver J P, Herzog E D, Hogenesch J B, Wozniak D F, Dikranian K, Giasson B I, Weaver D R, Holtzman D M, Fitzgerald G A. Circadian clock proteins regulate neuronal redox homeostasis and neurodegeneration. J Clin Invest. (2013) 123(12): 5389-5400.

(Non-patent document 26) Lauretti E, Di Meco A, Merali S, Pratico D. Circadian rhythm dysfunction: a novel environmental risk factor for Parkinson's disease. Mol Psychiatry. (2017) 22(2): 280-286.

(Non-patent document 27) Gorbacheva V Y, Kondratov R V, Zhang R, Cherukuri S, Gudkov A V, Takahashi J S, Antoch M P. Circadian sensitivity to the chemotherapeutic agent cyclophosphamide depends on the functional status of the CLOCK/BMAL1 transactivation complex. Proc Natl Acad Sci USA. (2005) 102(9): 3407-3412.

(Non-patent document 28) Ozturk N, Lee J H, Gaddameedhi S, Sancar A. Loss of cryptochrome reduces cancer risk in p53 mutant mice. Proc Natl Acad Sci USA. (2009) 106(8): 2841-2846.

(Non-patent document 29) van der Horst G T, Muijtjens M, Kobayashi K, Takano R, Kanno S, Takao M, de Wit J, Verkerk A, Eker A P, van Leenen D, Buijs R, Bootsma D, Hoeijmakers J H, Yasui A. Mammalian Cry1 and Cry2 are essential for maintenance of circadian rhythms. Nature. (1999) 398(6728): 627-630.

(Non-patent document 30) Chun S K, Chung S, Kim H D, Lee J H, Jang J, Kim J, Kim D, Son G H, Oh Y J, Suh Y G, Lee C S, Kim K. A synthetic cryptochrome inhibitor induces anti-proliferative effects and increases chemosensitivity in human breast cancer cells. Biochem Biophys Res Commun. (2015) 467(2): 441-446.

(Non-patent document 31) Yoo S H, Yamazaki S, Lowrey P L, Shimomura K, Ko C H, Buhr E D, Siepka S M, Hong H K, Oh W J, Yoo O J, Menaker M, Takahashi J S. PERIOD2::LUCIFERASE real-time reporting of circadian dynamics reveals persistent circadian oscillations in mouse peripheral tissues. Proc Natl Acad Sci USA. (2004) 101(15): 5339-5346.

DISCLOSURE OF INVENTION

Technical Goals

Under this background, the present inventors aimed to develop chemical compounds that act directly on the molecular circadian clockwork by use of a cell-based assay system measuring the activity of the CLOCK:BMAL1 heterodimer. Thus, the present inventors identified the oxyiminomethylbenzene derivative compounds, which enhance the cellular circadian rhythmicity as well as inhibit the negative feedback actions of CRY proteins on the CLOCK:BMAL1 heterodimer. Thus, the present disclosure was completed.

Therefore, an aspect of the present disclosure is to provide the oxyiminomethylbenzene derivative compounds and pharmaceutically acceptable salts thereof prepared using organic synthesis techniques.

Another aspect of the present disclosure is to provide a pharmaceutical composition for the prevention or treatment of circadian rhythm-related diseases, including the oxyiminomethylbenzene derivative or a pharmaceutically acceptable salt thereof as an active ingredient.

However, aspects of the present disclosure are not limited to the one set forth herein, and other aspects not mentioned herein would be clearly understood by one of ordinary skill in the art from the following description.

Technical Solutions

According to one example embodiment of the present disclosure, a pharmaceutical composition for preventing or treating circadian rhythm-related diseases is provided, including an oxyiminomethylbenzene derivative represented by following Chemical Formula 1 or a pharmaceutically acceptable salt thereof.

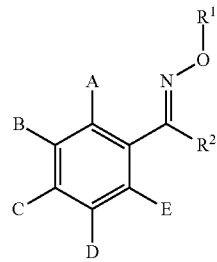

[Chemical Formula 1]

(in Chemical Formula 1, $R^1$ represents C1-C10 straight or branched chain alkyl; C4-C10 cycloalkyl; 5 to 7 membered substituted or unsubstituted aromatic group having carbon, oxygen, nitrogen, or sulfur added thereto, wherein the aromatic group represents a furanyl group, a thiophenyl group, a phenyl group, a thiazole group, an indole group, an isoindole group, a pyridinyl group, a piperazinyl group, a pyridazinyl group, a naphthyl group, a quinolinyl group, or an isoquinolinyl group, wherein a substituent represents 1 to 4 substituents selected from a group consisting of hydrogen, halogen, cyano, nitro, hydroxy, C1-C10 straight or branched chain alkyl, C1-C10 alkoxy, C1-C10 haloalkyl, C1-C10 haloalkoxy, C1-C10 alkylthio, C1-C10 alkyl carbonyl, and C1-C10 alkoxy carbonyl;

$R^2$ represents a substituent selected from a group consisting of a hydrogen atom; a C1-C10 straight or branched or cyclic alkyl group; and each of A, B, C, D, and E independently represents a substituent selected from a group consisting of hydrogen; halogen; cyano; nitro; hydroxy; C1-C10 straight or branched chain alkyl; C1-C10 alkoxy; C1-C10 haloalkyl; C1-C10 haloalkoxy; C1-C10 alkylthio; C1-C10 alkyl carbonyl; or a C1-C10 alkoxycarbonyl, wherein each of A, B, C, D, and E independently may include a straight-chain or branched C1-C10 alkyl or alkoxy carboxylic acid or an ester thereof).

According to an aspect, the oxyiminomethylbenzene derivative represented by Chemical Formula 1 may be one compound selected from a group consisting of:

1) methyl 2-{3-[N-{[3-(trifluoromethyl)phenyl]methoxyl}ethanimidoyl]phenoxy}acetate;
2) {3-[N-{[3-(trifluoromethyl)phenyl]methoxy}ethanimidoyl]phenoxy}acetic acid;
3) methyl 2-(3-{N-[(4-methoxyphenyl)methoxy]ethanimidoyl}phenoxy)acetate;
4) (3-{N-[(4-methoxy phenyl)methoxy]ethanimidoyl}phenoxy)acetic acid;
5) methyl 2-(3-{N-[(4-bromophenyl)methoxy]ethanimidoyl}phenoxy)acetate;
6) (3-{N-[(4-bromophenyl)methoxy]ethanimidoyl}phenoxy)acetic acid;
7) 2-{3-[N-(4-bromophenyl)methoxyethanimidoyl]phenoxyl}-N-[(pyridin-2-yl)methyl]acetamide;
8) 2-{3-[N-(4-bromophenyl)methoxyethanimidoyl]phenoxyl}-N-[2-(1H-imidazol-2-yl)ethyl]acetamide;
9) methyl 2-(3-{N-[(4-nitrophenyl)methoxy]ethanimidoyl}phenoxy)acetate;
10) (3-{N-[(4-nitrophenyl)methoxy]ethanimidoyl}phenoxy)acetic acid;
11) methyl 2-{3-[N-{[4-(methanesulfonyl)phenyl]methoxy}ethanimidoyl]phenoxy}acetate;

12) {3-[N-{[4-(methanesulfonyl)phenyl]methoxy}ethanimidoyl]phenoxy}acetic acid;
13) methyl 2-(3-{(N-[(4-fluorophenyl)methoxy]ethanimidoyl}phenoxy)acetate;
14) (3-{N-[(4-fluorophenyl)methoxy]ethanimidoyl}phenoxy)acetic acid;
15) methyl 2-{4-[N-{[3-(trifluoromethyl)phenyl]methoxy}ethanimidoyl]phenoxy}acetate;
16) {4-[N-{[3-(trifluoromethyl)phenyl]methoxy}ethanimidoyl]phenoxy}acetic acid;
17) methyl 2-(4-{N-[(4-methoxy phenyl)methoxy]ethanimidoyl}phenoxy)acetate;
18) (4-{N-[(4-methoxy phenyl)methoxy]ethanimidoyl}phenoxy)acetic acid;
19) methyl 2-(4-{N-[(4-bromophenyl)methoxy]ethanimidoyl}phenoxy)acetate;
20) (4-{N-[(4-bromophenyl)methoxy]ethanimidoyl}phenoxy)acetic acid;
21) 2-{4-[N-(4-bromophenyl)methoxyethanimidoyl]phenoxy}-N-[(pyridin-2-yl)methyl]acetamide;
22) 2-{4-[N-(4-bromophenyl)methoxyethanimidoyl]phenoxy}-N-[2-(1H-imidazol-2-yl)ethyl]acetamide;
23) methyl 2-(4-{N-[(4-nitrophenyl)methoxy]ethanimidoyl}phenoxy)acetate;
24) (4-{N-[(4-nitrophenyl)methoxy]ethanimidoyl}phenoxy)acetic acid;
25) methyl 2-{4-[N-{[4-(methanesulfonyl)phenyl]methoxy}ethanimidoyl]phenoxy}acetate; and
26) {4-[N-{[4-(methanesulfonyl)phenyl]methoxy}ethanimidoyl]phenoxy}acetic acid.

According to an aspect, the circadian rhythm-related disease may be sleep disorder, metabolic disorder, cardiovascular disease, immune and inflammatory disease, mood disorder, addiction disorder, neurodegeneration or cancer.

According to an aspect, the sleep disorder may be jet lag syndrome, shift work sleep disorder, progressive sleep phase syndrome, sleep phase delay syndrome, respiratory related sleep disorder, restless legs syndrome, or REM sleep behavior disorder.

According to an aspect, the metabolic disorder may be obesity, hypertension, hyperlipidemia, hyperglycemia, or polyuria.

According to an aspect, the mood disorder may be depression, bipolar mood disorder, seasonal disorder, or anxiety disorder.

According to an aspect, the degenerative brain disease may be Alzheimer's disease, Parkinson's disease, Huntington's disease, or dementia disease.

According to an aspect, the cardiovascular disease may be ischemic heart disease, acute myocardial infarction, cerebral infarction, or atrial fibrillation.

According to an aspect, the cancer may be colon cancer, stomach cancer, prostate cancer, breast cancer, kidney cancer, liver cancer, lung cancer, uterine cancer, colon cancer, pancreatic cancer, ovarian cancer, blood cancer, or brain tumor.

According to an aspect, the oxyiminomethylbenzene derivative represented by Chemical Formula 1 may enhance an amplitude of the circadian molecular rhythm and stabilize a period thereof by inhibiting the negative feedback actions of CRYs on transcriptional activity of CLOCK:BMAL1 heterodimer.

Effects of the Invention

The oxyiminomethylbenzene derivative of the present disclosure may enhance or strengthen the rhythmicity of the circadian molecular clock by inhibiting the feedback actions of CRY and thereby promoting the activity of the CLOCK:BMAL1 heterodimer. Therefore, the pharmaceutical composition including the oxyiminomethylbenzene derivative of the present disclosure or a pharmaceutically acceptable salt thereof as an active ingredient may be usefully used in the prevention or treatment of the circadian rhythm-related diseases such as sleep disorders, metabolic diseases, cardiovascular diseases, immune and inflammatory diseases, mood disorders, neurodegenerative diseases and cancer.

It should be understood that the effect of the present disclosure is not limited to the above effect, and rather includes all effects that may be inferred from the detailed description of the present disclosure or the configuration of the present disclosure described in the claims.

BRIEF DESCRIPTION OF DRAWINGS

FIG. 3A identifies the effect of the compounds of Chemical Formula 8-9 and 8-10 and KS15 on the rhythmic expression of the PER2-LUC fusion protein. FIG. 3B identifies results of statistical analysis of the effect of the compounds of Chemical Formula 8-9 and 8-10 and KS15 on the amplitude (Amplitude, left), period (Period, middle) and robustness (Robustness, right) of the rhythm found in the expression of the PER2-LUC fusion protein.

BEST MODE FOR CARRYING OUT THE INVENTION

Figure 1:
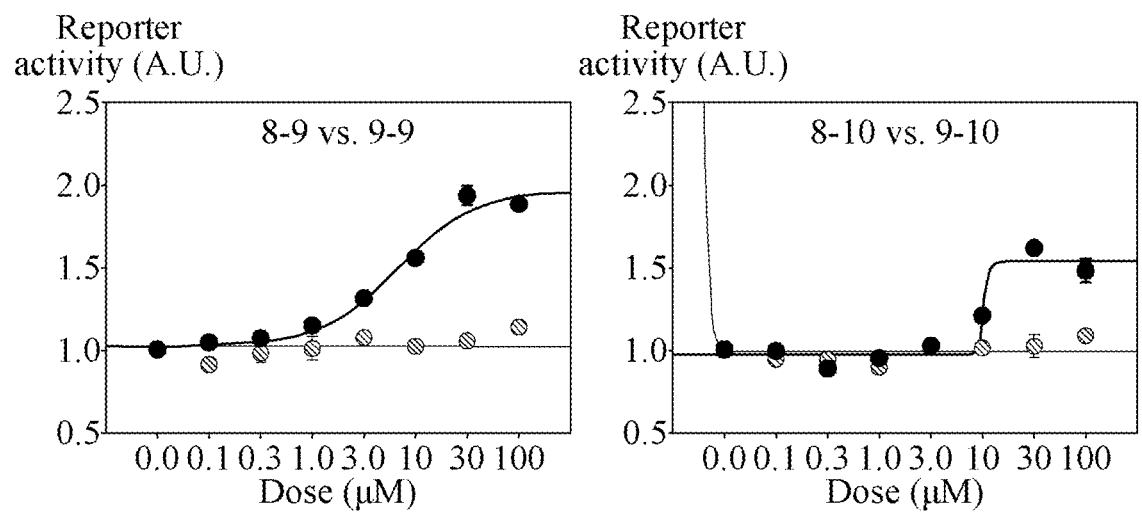
FIG. 1 shows an evaluation of the concentration-dependent effect of compounds of Chemical Formula 8-9, 9-9, 8-10 and 9-10 among the oxyiminomethylbenzene derivatives on the luciferase reporter (E-box-LUC) measuring the activity of the CLOCK:BMAL1 dimer, wherein compounds of Chemical Formula 8-9 and 8-10 increase the activity of E-box-LUC in a concentration-dependent manner.

Hereinafter, example embodiments will be described in detail with reference to the accompanying drawings. However, since various changes may be made to the example embodiments, the scope of the patent application is not limited or restricted by these example embodiments. It should be understood that all changes, equivalents, or substitutes for the example embodiments are included in the scope of the rights of the disclosure.

The terminology used herein is for illustrative purposes only and is not intended to be limiting of the present disclosure. As used herein, singular forms are intended to include the plural forms as well, unless the context clearly indicates otherwise. It will be further understood that the terms "comprises", "comprising", "includes", and "including" when used in this specification, specify the presence of the stated features, integers, operations, elements, components, portions thereof, or a combination thereof, but do not preclude the presence or addition of one or more other features, integers, operations, elements, components, portions thereof, or a combination thereof.

Unless otherwise defined, all terms including technical and scientific terms used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In addition, in the description with reference to the accompanying drawings, the same reference numerals are assigned to the same components regardless of the reference numerals, and redundant descriptions thereof will be omitted. In describing the example embodiments, when it is determined that a detailed description of related known technologies may unnecessarily obscure the gist of the example embodiments, the detailed description thereof will be omitted.

According to an example embodiment of the present disclosure, a pharmaceutical composition for preventing or treating circadian rhythm-related diseases is provided, the composition including an oxyiminomethylbenzene derivative represented by following Chemical Formula 1 or a pharmaceutically acceptable salt thereof.

[Chemical Formula 1]

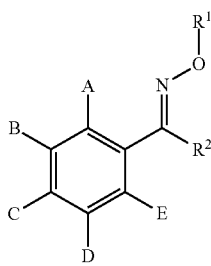

(in Chemical Formula 1, $R^1$ represents C1-C10 straight or branched chain alkyl; C4-C10 cycloalkyl; 5 to 7 membered substituted or unsubstituted aromatic group having carbon, oxygen, nitrogen, or sulfur added thereto, wherein the aromatic group represents a furanyl group, a thiophenyl group, a phenyl group, a thiazole group, an indole group, an isoindole group, a pyridinyl group, a piperazinyl group, a pyridazinyl group, a naphthyl group, a quinolinyl group, or an isoquinolinyl group, wherein a substituent represents 1 to 4 substituents selected from a group consisting of hydrogen, halogen, cyano, nitro, hydroxy, C1-C10 straight or branched chain alkyl, C1-C10 alkoxy, C1-C10 haloalkyl, C1-C10 haloalkoxy, C1-C10 alkylthio, C1-C10 alkyl carbonyl, and C1-C10 alkoxy carbonyl;

$R^2$ represents a substituent selected from a group consisting of a hydrogen atom; a C1-C10 straight or branched or cyclic alkyl group; and each of A, B, C, D, and E independently represents a substituent selected from a group consisting of hydrogen; halogen; cyano; nitro; hydroxy; C1-C10 straight or branched chain alkyl; C1-C10 alkoxy; C1-C10 haloalkyl; C1-C10 haloalkoxy; C1-C10 alkylthio; C1-C10 alkyl carbonyl; or a C1-C10 alkoxycarbonyl, wherein each of A, B, C, D, and E independently may include a straight-chain or branched C1-C10 alkyl or alkoxy carboxylic acid or an ester thereof).

More specifically, the oxyiminomethylbenzene derivative represented by Chemical Formula 1 may be one compound selected from a group consisting of:

1) methyl 2-{3-[N-{[3-(trifluoromethyl)phenyl]methoxy}ethanimidoyl]phenoxy}acetate;
2) {3-[N-{[3-(trifluoromethyl)phenyl]methoxy}ethanimidoyl]phenoxy}acetic acid;
3) methyl 2-(3-{N-[(4-methoxy phenyl)methoxy]ethanimidoyl}phenoxy)acetate;
4) (3-{N-[(4-methoxy phenyl)methoxy]ethanimidoyl}phenoxy)acetic acid;
5) methyl 2-(3-{N-[(4-bromophenyl)methoxy]ethanimidoyl}phenoxy)acetate;
6) (3-{N-[(4-bromophenyl)methoxy]ethanimidoyl}phenoxy)acetic acid;
7) 2-{3-[N-(4-bromophenyl)methoxyethanimidoyl]phenoxy}-N-[(pyridin-2-yl)methyl]acetamide;
8) 2-{3-[N-(4-bromophenyl)methoxyethanimidoyl]phenoxy}-N-[2-(1H-imidazol-2-yl)ethyl]acetamide;
9) methyl 2-(3-{N-[(4-nitrophenyl)methoxy]ethanimidoyl}phenoxy)acetate;
10) (3-{N-[(4-nitrophenyl)methoxy]ethanimidoyl}phenoxy)acetic acid;
11) methyl 2-{3-[N-{[4-(methanesulfonyl)phenyl]methoxy}ethanimidoyl]phenoxy}acetate;
12) {3-[N-{[4-(methanesulfonyl)phenyl]methoxy}ethanimidoyl]phenoxy}acetic acid;
13) methyl 2-(3-{(N-[(4-fluorophenyl)methoxy]ethanimidoyl}phenoxy)acetate;
14) (3-{N-[(4-fluorophenyl)methoxy]ethanimidoyl}phenoxy)acetic acid;
15) methyl 2-{4-[N-{[3-(trifluoromethyl)phenyl]methoxy}ethanimidoyl]phenoxy}acetate;
16) {4-[N-{[3-(trifluoromethyl)phenyl]methoxy}ethanimidoyl]phenoxy}acetic acid;
17) methyl 2-(4-{N-[(4-methoxy phenyl)methoxy]ethanimidoyl}phenoxy)acetate;
18) (4-{N-[(4-methoxyphenyl)methoxy]ethanimidoyl}phenoxy)acetic acid;
19) methyl 2-(4-{N-[(4-bromophenyl)methoxy]ethanimidoyl}phenoxy)acetate;
20) (4-{N-[(4-bromophenyl)methoxy]ethanimidoyl}phenoxy)acetic acid;
21) 2-{4-[N-(4-bromophenyl)methoxyethanimidoyl]phenoxy}-N-[(pyridin-2-yl)methyl]acetamide;
22) 2-{4-[N-(4-bromophenyl)methoxyethanimidoyl]phenoxy}-N-[2-(1H-imidazol-2-yl)ethyl]acetamide;
23) methyl 2-(4-{N-[(4-nitrophenyl)methoxy]ethanimidoyl}phenoxy)acetate;
24) (4-{N-[(4-nitrophenyl)methoxy]ethanimidoyl}phenoxy)acetic acid;
25) methyl 2-{4-[N-{[4-(methanesulfonyl)phenyl]methoxy}ethanimidoyl]phenoxy}acetate; and
26) {4-[N-{[4-(methanesulfonyl)phenyl]methoxy}ethanimidoyl]phenoxy}acetic acid.

The oxyiminomethylbenzene derivative represented by Chemical Formula 1 of the present disclosure may include pharmaceutically acceptable salts, hydrates and solvates thereof.

In the present specification, when referring to a compound represented by Chemical Formula 1, it may be understood that the compound is intended to include a pharmaceutically acceptable salt thereof. Such a pharmaceutically acceptable salt may be prepared by a method for preparing a salt that is commonly used.

The 'pharmaceutically acceptable salt' refers to a salt prepared from a pharmaceutically acceptable non-toxic base or acid including an inorganic or organic base and an inorganic or organic acid. Salts derived from inorganic bases include aluminum, ammonium, calcium, copper, ferric, ferrous, lithium, magnesium, manganese salts, manganese, potassium, sodium, zinc, and the like. In particular, ammonium, calcium, magnesium, potassium or sodium salts are preferred. Solid salts may exist in one or more crystal structures, or may also exist in a hydrate form. Salts derived from pharmaceutically acceptable non-toxic organic bases include a basic ion exchange resin such as primary, secondary or tertiary amines, substituted amines including naturally substituted amines, amine ring, or arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropyl amine, lysine, methylglucamine, porpoline, piperazine, piperidine, polyamine resin, procaine, purine, theobromine, triethylamine, trimethylamine, tripropylamine, tromethamine, and the like.

When the compound according to the present disclosure is basic, the salt may be prepared from a pharmaceutically acceptable non-toxic acid including inorganic and organic acids. The acid may include acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, maleic acid, malic acid, mandelic acid, methanesulfonic acid, muxic acid, nitric acid, pamoic acid, pantothenic acid, phosphoric acid, succinic acid, sulfuric acid, tartaric acid, p-toluene sulfonic acid, etc. The citric acid, hydrobromic acid, hydrochloric acid, maleic acid, phosphoric acid, sulfuric acid, fumaric acid or tartaric acid are particularly preferred.

A hydrate of the oxyiminomethylbenzene derivative compound represented by Chemical Formula 1 of the present disclosure or a pharmaceutically acceptable salt thereof may be understood as including a stoichiometric or non-stoichiometric amount of water bound via a non-covalent intermolecular force. The hydrate may contain at least 1 equivalent, generally 1 to 5 equivalents of water. Such a hydrate may be prepared by crystallizing a compound represented by Chemical Formula 1 of the present disclosure or a pharmaceutically acceptable salt thereof from water or a solvent containing water.

It will be understood that the solvate of the oxyiminomethylbenzene derivative compound represented by Chemical Formula 1 of the present disclosure or a pharmaceutically acceptable salt thereof includes a stoichiometric or non-stoichiometric amount of a solvent bonded via a non-covalent intermolecular force. The solvent may preferably include volatile, non-toxic, or suitable solvents for administration to humans.

The pharmaceutical composition according to the present disclosure contains the oxyiminomethylbenzene derivative compound represented by Chemical Formula 1 as an active ingredient. Formulations conventional in the pharmaceutical field, that is, formulation for oral administration or parenteral administration such as tablets, capsules, troches, solutions, suspensions, etc., may be formulated by adding the usual non-toxic pharmaceutically acceptable carriers, adjuvants, excipients, etc.

Excipients that may be used in the pharmaceutical composition according to the present disclosure may include sweeteners, binders, solubilizers, dissolvents, wetting agents, emulsifiers, isotonic agents, adsorbents, disintegrants, antioxidants, preservatives, lubricants, fillers, and fragrances. For example, the excipients may include lactose, dextrose, sucrose, mannitol, sorbitol, cellulose, glycine, silica, talc, stearic acid, stearic acid, magnesium stearate, magnesium aluminum silicate, starch, gelatin, tragacanth rubber, arginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, and the like.

The pharmaceutical composition according to the present disclosure is administered in a pharmaceutically effective amount. In the present disclosure, the term "pharmaceutically effective amount" means an amount sufficient to treat a disease at a reasonable benefit/risk ratio applicable to medical treatment. The effective dose level depends on factors including the type of disease, the severity thereof, the activity of the drug, the sensitivity to the drug, the time of administration, the route of administration and the rate of excretion, the treatment period, and drugs used concurrently, and other factors well known in the medical field. The pharmaceutical composition according to the present disclosure may be administered as an individual therapeutic agent or administered in combination with other therapeutic agents, and may be administered sequentially or simultaneously with conventional therapeutic agents, or may be administered in a single or multiple times. It is important to take into account all of the above factors to administer the amount that may obtain the maximum effect in the minimum amount without side effects. This may be easily determined by a person skilled in the art.

Specifically, the effective amount of the pharmaceutical composition according to the present disclosure may vary depending on the patient's age, sex, condition, weight, absorption of the active ingredient in the body, the inactivation rate and excretion rate, the type of disease, and the drug used in combination therewith. In general, the effective amount of the pharmaceutical composition may be administered in an amount of 0.1 mg/kg to 100 mg/kg per day, preferably 1 to 30 mg/kg. The pharmaceutical composition may be administered once or several times a day.

The pharmaceutical composition according to the present disclosure may be administered to a subject via various routes. All modes of administration may be expected. For example, the composition may be administered via oral, rectal, intravenous, intramuscular, subcutaneous, intrauterine, dural or cerebrovascular injection. The administration routes of the pharmaceutical composition according to the present disclosure may be determined based on the type of drug as the active ingredient, along with a number of related factors such as the disease to be treated, the route of administration, the age, sex and weight of the patient, and the severity of the disease.

The pharmaceutical composition according to the present disclosure inhibits the activity of the CRY molecule, such that the circadian rhythm of the molecular biological clock may be enhanced. Therefore, the pharmaceutical composition according to the present disclosure contains the oxyiminomethylbenzene derivative compound and a pharmaceutically acceptable salt thereof as an active ingredient. The derivatives may be usefully used in the treatment of circadian rhythm-related diseases through the inhibitory effect of CRY activity or the improvement effect of the circadian rhythm of the molecular biological clock core loop.

The circadian rhythm-related diseases may include, but is not limited to, sleep disorder, metabolic disease, cardiovascular disease, immune and inflammatory disease, mood disorder, addiction disorder, neurodegenerative disease, and cancer.

In the present disclosure, the term "circadian rhythm-related disease" refers to a disease that occurs due to a cause of various physiological and mental abnormalities due to the disruption of the circadian rhythm or clock by genetic or environmental factors. Examples of circadian rhythm-related diseases include sleep disorders including jet lag and shift work syndrome, metabolic disorders including obesity and diabetes, cardiovascular disease, immune and inflammatory diseases, mood disorders, neurodegenerative diseases and cancer. In addition, the types of diseases are very diverse. These diseases may be prevented or treated by modulating the circadian rhythm biological clock molecular network.

For example, the pharmaceutical composition according to the present disclosure is effective as an agent for prevention, control or treatment of circadian rhythm-related diseases such as sleep disorders, metabolic diseases, cardiovascular diseases, immune and inflammatory diseases, mood disorders, neurodegenerative diseases and cancer.

In addition, the pharmaceutical composition according to the present disclosure may be solely used or may be used in combination with methods using surgery, hormone therapy, drug based treatment, and biological response modifiers, for the prevention and treatment of diseases such as sleep disorders, metabolic diseases, cardiovascular diseases, immune and inflammatory diseases, mood disorders, neurodegenerative diseases and cancer.

In the present disclosure, the term "circadian rhythm-related sleep disorder" refers to a disorder in which the sleep/wake rhythm occurs in an abnormal pattern due to genetic or environmental disturbances applied to the biological clock. Patients with sleep disorders may have difficulty falling asleep or waking up at a socially necessary time, and may complain of a disorder caused by lack of sleep. Regarding a cause of onset thereof, sleep disorders caused by CRY as a downstream gene of the biological clock network have been reported. According to a recent genetic study of sleep disorder patients, in a genetic study of sleep disorder patients who sleep excessively during the daytime, the genetic polymorphism of rs17289712 present in the intron of the CRY1 gene has significant relation with the symptoms of this disease. This means that CRY plays a unique role in the regulation of sleep/wake rhythm by the biological clock (Non-patent document 8).

On the other hand, in another study to investigate the effect of CRY as a downstream gene of the biological clock on sleep, mice that lack both CRY1 and CRY2 genes have increased non-REM sleep (NREMS) compared to normal mice. During non-REM sleep, the intensity of delta waves tended to increase (Non-patent document 9). This means increased deep sleep. This sleep pattern of mice lacking the CRY1 and CRY2 genes is different from the symptoms seen in the animal model in which the circadian rhythm was disrupted by artificially destroying the suprachiasmatic nucleus (SCN) in the hypothalamus. When the suprachiasmatic nucleus (SCN) of the mouse is destroyed, there is no change in the total sleep time, but the sleep pattern is fragmented and the intensity of the delta wave tends to decrease (Non-patent document 10). This suggests the possibility that CRY may have an independent role in the regulation of sleep homeostasis apart from the role that CRY plays in the circadian rhythm biological clock.

Therefore, to verify the regulation of CRY protein activity by the oxyiminomethylbenzene derivative represented by Chemical Formula 1 according to the present disclosure, Experimental Examples 1 to 3 shown below were conducted. Based on the experiment results, the oxyiminomethylbenzene derivative compound not only has excellent inhibitory efficacy against CRY protein which inhibits the activity of CLOCK:BMAL1 dimer, but also increases the amplitude of the circadian molecular rhythm at the cellular level as measured by the cyclic expression of the PER2-LUC fusion protein and has the effect of enhancing activity thereof. Therefore, the pharmaceutical composition including the oxyiminomethylbenzene derivative represented by Chemical Formula 1 of the present disclosure or a pharmaceutically acceptable salt thereof as an active ingredient may prevent or treat the circadian rhythm-related sleep disorders related to the core genes of the biological clock.

Studies have been reported which showed that metabolic disorders as one of the disorders associated with the circadian rhythm, may be caused by functional abnormalities of the biological clock due to genetic or environmental causes. Abnormal lifestyle patterns, such as long shift work or lack of sleep may slow down the circadian rhythm of secretion of growth hormone and melatonin in the body and may increase cortisol levels (Non-patent document 11). These hormonal changes lead to weight gain similar to the initial symptoms of obesity.

In addition, the relationship between the circadian clock system and metabolic disorders is more evident through the analysis results of genetically engineered animal models. It has been found that hyper leptin and insulin secretion are reduced in CLOCK mutant mice. Symptoms of hyperlipidemia and hyperglycemia occurred in the mice (Non-patent document 12). In addition, the BMAL1 gene deficient mice showed impairment in the growth and differentiation of adipocytes. Abnormal symptoms were also found in the metabolism of carbohydrates in the liver (Non-patent documents 13 to 15). In addition, recent studies have revealed that CRY functions as an important regulator in the process of gluconeogenesis in the liver, which is the cause of hyperglycemia. In mice lacking the CRY, abnormalities in blood sugar control were observed compared to normal mice. This was found to be because CRY binds to the glucocorticoid receptor (GR) and regulates the expression of gluconeogenesis genes via the hormone (Non-patent document 16). In addition, CRY may bind not only to GR, but also to the G subunit, which is one of the components of the G-protein coupled receptor to regulate the activity of adenyl cyclase. Thus, the CRY has the effect of regulating the expression of genes that play a role in the gluconeogenesis induced by cyclic adenosine monophosphate (cAMP) (Non-patent document 17).

This is a study result showing more clearly that metabolic disorders are not only related to the phase shift of the biological clock, but also that deficiency of CLOCK, BMAL1, and abnormal expression of CRY1 may cause metabolic disorders. In addition, these results suggest that the expression of CLOCK and BMAL1 and the enhancement of the activity of the CLOCK:BMAL1 dimer and inhibition of the activity of CRY are effective for treatment.

Therefore, in order to identify the effect of enhancing the activity of CLOCK:BMAL1 dimer and inhibiting CRY activity by the oxyiminomethylbenzene derivative represented by Chemical Formula 1 according to the present disclosure, Experimental Examples 1 to 3 were conducted.

As a result, the oxyiminomethylbenzene derivative not only has excellent inhibitory efficacy against CRY protein which inhibits the activity of CLOCK:BMAL1 dimer, but also increases the amplitude of the circadian molecular rhythm at the cellular level as measured by the cyclic expression of the PER2-LUC fusion protein, and thus has an excellent effect of enhancing the activity thereof.

Therefore, the pharmaceutical composition containing the oxyiminomethylbenzene derivative represented by Chemical Formula 1 according to the present disclosure or acceptable salts thereof may be usefully used in the prevention or treatment of the metabolic diseases caused by functional disturbance of the biological clock.

The metabolic disease associated with the circadian rhythm may be obesity, hypertension, hyperlipidemia, hyperglycemia, or polyuria, but is not limited thereto.

Mood disorders and addiction disorders may also develop due to alteration of the circadian rhythm. Researches thereon are being actively conducted. Like physical functions such as metabolic activity and cell division, emotional change as one of the higher functions of the brain exhibits a circadian rhythm. The biological clock is responsible for the onset and progression of various types of mood disorders showing pathological symptoms in the regulation of the emotions.

In order to find out the relationship between mood disorders and circadian clock, blood samples in 30 people with major depression and 30 people without disability were analyzed to evaluate the mRNA expression patterns associated with the four circadian rhythm genes. mRNA represents gene activity. Participants with a history of depression had a higher CLOCK gene activity than those without depression. Thus, it may be predicted that depressive disorder is related to the activity of CLOCK as a key gene in the biological clock (Non-patent document 18).

Among the mood disorders, bipolar mood disorder, or manic depression has the most remarkable association with the biological clock. In gene targeting mice to various circadian clock genes such as Clock, Rev-erbα, Per, Cry, etc., a behavioral phenotype similar to manic depression occurs (Non-patent documents 19 to 21). Especially, before the occurrence of manic episodes in patients with manic depression, modulation of the phase of the circadian rhythm biological rhythms occurs (Non-patent document 22). These results strongly suggest that the weakening of the activity and robustness of the circadian rhythm biological clock is a key mechanism for the onset of manic depression.

In addition, the relationship between the biological clock and mood disorders may be identified via light therapy. Light therapy as one of the methods widely used among methods of treating mood disorders through artificial stimulation that may control the biological clock in addition to drug treatment is known to be particularly effective in seasonal mood disorders. Seasonal mood disorder is one of the most common mental disorders in which 5 to 10% of the population living in a temperate climate zone with four seasons exhibits symptoms thereof. The symptoms similar to depression occur in winter when the sun rises later and the daylight is shortened. At this time, when a patient with seasonal mood disorder is artificially exposed to strong light, the symptoms of depression are alleviated. Light therapy performed in the early morning is more effective than in the evening (Non-patent document 23). This indicates not only that the symptoms of seasonal mood disorder are related to the phase modulation of the biological clock, but also that the expression of CLOCK and BMAL1 which are the key genes of the biological clock that are activated during the daytime when there is light, and the activity of the CLOCK:BMAL1 dimer work in the treatment.

In consideration of these facts, the effect of enhancing the activity of the CLOCK:BMAL1 dimer and the circadian molecular rhythm by the oxyiminomethylbenzene derivative compound represented by Chemical Formula 1 of the present disclosure were identified. Based on a result of performing the experiments of Experimental Examples 1 to 3, the oxyiminomethylbenzene derivative not only has excellent inhibitory efficacy against CRY protein which inhibits the activity of CLOCK:BMAL1 dimer, but also increases the amplitude of the circadian molecular rhythm at the cellular level as measured by the cyclic expression of the PER2-LUC fusion protein, and thus has an excellent effect of enhancing the activity thereof. Therefore, the pharmaceutical composition containing the oxyiminomethylbenzene derivative represented by Chemical Formula 1 of the present disclosure or the pharmaceutically acceptable salts thereof may be useful for preventing or treating mood disorder-related diseases via pharmacological control of the circadian rhythm biological clock.

In this connection, the circadian rhythm-related mood disorder may typically be major depression, bipolar mood disorder, seasonal disorder, or anxiety disorder, but is not limited thereto.

Various degenerative brain diseases may also develop due to changes in the circadian rhythm. Researches thereon are being actively conducted. Abnormalities in the circadian rhythm biorhythms including sleep disorders, have been reported since the early onset in patients with various degenerative brain diseases such as Alzheimer's disease, Parkinson's disease, and Huntington's disease (Non-patent document 24). This is the main cause of degrading the life quality of the patient having degenerative brain diseases. In particular, circadian rhythm abnormalities and related sleep disorders are sometimes considered as representative non-motor symptoms in Parkinson's disease and Huntington's disease. In the latest research using animal models, weakening the activity of the biological clock increases the risk of developing degenerative brain diseases and is a major etiology for worsening symptoms (Non-patent documents 25 to 26).

Considering these facts, Experimental Examples 1 and 3 were performed to identify the effect of enhancing the activity of the dimer of CLOCK:BMAL1 and the effect of enhancing the circadian rhythm molecular biorhythm by the oxyiminomethylbenzene derivative compound represented by Chemical Formula 1 according to the present disclosure. As a result, it was identified that the oxyiminomethylbenzene derivative compound enhances the activity of the CLOCK:BMAL1 dimer and increases the amplitude of circadian rhythm PER-LUC fusion protein expression and thus strengthens the molecular circadian rhythm. Therefore, the pharmaceutical composition containing the oxyiminomethylbenzene derivative or the pharmaceutically acceptable salts thereof in accordance with the present disclosure may be usefully used to prevent or treat the diseases related to neurodegenerative diseases through pharmacological control of the circadian rhythm biological clock.

In this case, the circadian rhythm-related neurodegenerative disease may be Alzheimer's disease, Parkinson's disease, or Huntington's disease, but is not limited thereto.

In the cancer as one of the circadian rhythm-related diseases, the circadian rhythm change in the susceptibility to anticancer drugs clearly shows the relationship between the key genes of the biological clock and tumors. CRY gene targeting mice showed higher anticancer drug resistance than in normal mice at all times. The difference in resistance is because the functional state of CLOCK:BMAL1 dimer in hepatocytes is different between the normal mice and circadian rhythm genetically engineered mice, and thus, the difference in the liver's ability to treat toxicity of anticancer drugs occurs (Non-patent document 27). This study shows that the CLOCK:BMAL1 dimer as a key gene in the biological period, and CRY as the downstream gene thereof have a great influence on the effect on anticancer drugs.

In addition to affecting the circadian rhythm changes in susceptibility to anticancer drugs, the circadian clock gene has the effect of more directly inhibiting the formation and growth of tumors. In the p53 gene-deficient mice as one of the animal models for tumor induction, tumor formation and growth were inhibited when CRY was additionally deleted (Non-patent document 28). Because CRY's gene defect completely destroys the subject's intrinsic circadian rhythm (Non-patent document 29), the disturbance of the biological clock and the pathway leading to tumor development do not necessarily coincide with each other, and more complex correlations therebetween may exist.

In particular, this suggests the possibility that the core genes of the biological clock have independent functions in the cell period and tumor development process, as well as in maintaining the circadian rhythm and provides the possibility of consideration of the new possibilities which temporary inhibition of CRY has in the anticancer action. In fact, KS15 as a persistent CRY inhibitor has insignificant effect of enhancing the circadian rhythm biorhythm but has anticancer effects against breast cancer cell lines (Non-patent document 30).

The oxyiminomethylbenzene derivative compound represented by Chemical Formula 1 of the present disclosure is excellent in inhibiting the action of CRY as shown in Experimental Example 1. Thus, the oxyiminomethylbenzene derivative compound has the pharmacological control of CRY activity, thereby increasing the efficacy of the drug and reducing toxicity through the drug limited to a specific time period. In addition, since the oxyiminomethylbenzene derivative compound inhibits the generation and growth of tumor cells, the pharmaceutical composition containing the same as an active ingredient may be usefully used in the prevention or treatment of cancer as caused by alteration of the circadian rhythm.

In this connection, the circadian rhythm-related cancer may be colon cancer, gastric cancer, prostate cancer, breast cancer, kidney cancer, liver cancer, lung cancer, uterine cancer, colon cancer, pancreatic cancer, ovarian cancer, blood cancer, or brain tumor, but is not limited thereto.

The method for preparing the oxyiminomethylbenzene derivative represented by Chemical Formula 1 of the present disclosure is as follows.

[Reaction Formula 1]

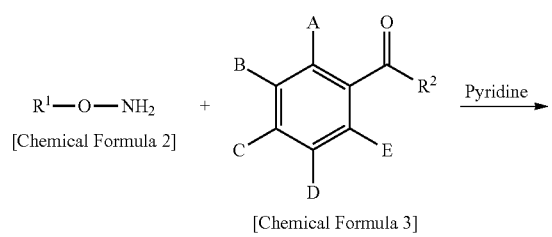

[Chemical Formula 3]

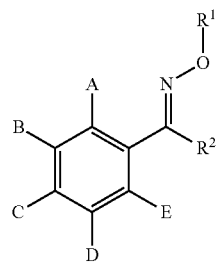

[Chemical Formula 1]

(In Reaction Formula 1, each of A to E, R1, and R2 are the same as defined above).

More specifically, an amine compound or a salt thereof substituted with R1 as represented by Chemical Formula 2 which may be typically obtained, and an aldehyde or a ketone compound substituted with A to E, and R2 as represented by Chemical Formula 3 which may be obtained normally may reach with each other to synthesize the oxyiminomethyl compound represented by Chemical Formula 1.

Hereinafter, desirable examples are presented to help understanding the present disclosure. However, the following examples are only provided for the skilled person to the art to more easily understand the present disclosure, and the content of the present disclosure is not limited to the following examples.

Example 1: Synthesis of Oxyiminomethylbenzene Derivative Compounds (Chemical Formula 8-9, and Chemical Formula 8-10 Compounds)

[Reaction Formula 2]

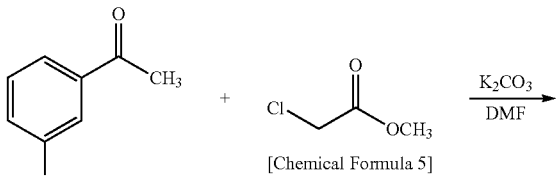

[Chemical Formula 4]     [Chemical Formula 5]

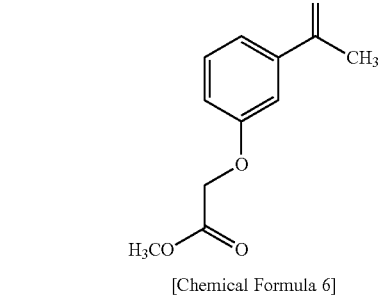

[Chemical Formula 6]

Step 1: Preparation of Acetophenone Derivatives (Chemical Formula 6)

As described in Reaction Formula 2, commercially available 3-hydroxyacetophenone (Chemical Formula 4, 1 g) was put into a reactor, and N,N-dimethylformaldehyde was added thereto. After cooling the reactor to 0° C., potassium carbonate (3 eq, 3 g) and methylchloroacetate (Chemical Formula 5, 1.2 equivalents, 0.767 ml) were slowly added thereto. The temperature of the reaction solution was raised to room temperature and the reaction solution was stirred for 12 hours. After completion of the reaction, the reaction solution was filtered and the filtrate was concentrated under reduced pressure. The concentrated compound was subjected to silica gel chromatography using ethyl acetate and n-hexane as mobile phases to obtain a target compound, that is, acetophenone derivative (Chemical Formula 6, 1453 mg, yield 95%).

1H-NMR (CDCl3, 500 MHz) δ 7.60 (m, 1H), 7.48 (m, 1H), 7.40 (dd, J=8.1, 7.5 Hz, 1H), 7.15 (m, 1H), 4.70 (s, 2H), 3.82 (s, 3H), 2.60 (s, 3H).

[Reaction Formula 3]

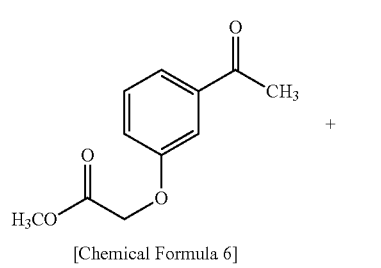

[Chemical Formula 6]

[Chemical Formula 7]

[Chemical Formula 8-9]

Step 2: Preparation of Oxyiminomethylbenzene Derivative Compounds (Chemical Formula 8-9)

As described in Reaction Formula 3, acetophenone derivatives (Chemical Formula 6, 208 mg) and a commercially available alkoxyamine compound (Chemical Formula 7, 1.2 equivalents, 246 mg) were put into a reactor, and pyridine was added thereto. The reaction solution was stirred for 5 hours while heating the reaction solution for reflux. After completion of the reaction, the reaction solution was cooled to room temperature and concentrated under reduced pressure. The concentrated compound was subjected to silica gel chromatography using ethyl acetate and n-hexane as mobile phases to obtain a target compound, that is, the oxyiminomethylbenzene derivative compound (Chemical Formula 8-9, 197 mg, yield 55%).

[Reaction Formula 4]

[Chemical Formula 8-9]

[Chemical Formula 8-10]

Step 3: Preparation of Oxyiminomethylbenzene Derivative Hydrolyzates (Chemical Formula 8-10)

As shown in Reaction Formula 4, the oxyiminomethylbenzene derivative compound (Chemical Formula 8-9, 20 mg) was added to a reactor, and then tetrahydrofuran, water, and methanol were added thereto. After cooling the reactor to 0° C., lithium hydroxide (3 equivalents, 7 mg) was slowly added thereto, and the temperature of the reaction solution was raised to room temperature, followed by stirring for 8 hours. After completion of the reaction, the reaction solution was neutralized with diluted hydrochloric acid and concentrated under reduced pressure. The residue was diluted with ethyl acetate, washed with water, dried using anhydrous magnesium sulfate, and filtered. The filtrate was concentrated under reduced pressure and subjected to silica gel chromatography using ethyl acetate and n-hexane as mobile phases to obtain a target compound, that is, the oxyiminomethylbenzene derivative hydrolyzate (Chemical Formula 8-10, 19 mg, yield 99%).

The same process was carried out in the same manner as in Example 1 above, except that A to E, $R^1$, and $R^2$ as used in the compound represented by Chemical Formula 1 were used as shown in the following [Table 1], such that the oxyiminomethylbenzene derivatives (Chemical Formula 8-1 to 14, 9-1 to 12) including hydrolyzate were synthesized. The structure and analysis results of the synthesized oxyiminomethylbenzene derivative compounds are summarized in the following [Table 1].

TABLE 1

| Compound | R³ | R⁴ | R⁵ | Analysis data (1H/13C-NMR or LC-MS) | Max (%) | EC₅₀ |
|---|---|---|---|---|---|---|

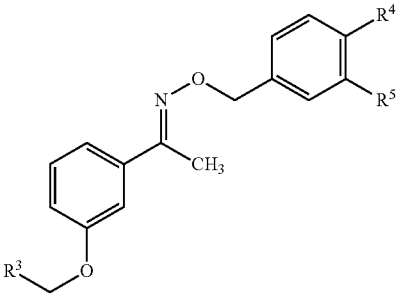

[Chemical Formula 8]

| Compound | R³ | R⁴ | R⁵ | Analysis data (1H/13C-NMR or LC-MS) | Max (%) | EC₅₀ |
|---|---|---|---|---|---|---|
| 8-1 | CO₂CH₃ | H | CF₃ | 1H-NMR (500 MHz, CDCl3) δ 7.56 (d, J = 8.0 Hz, 1H), 7.49 (t, J = 7.5 Hz, 2H), 7.29 (t, J = 8.0 Hz, 1H), 7.26 (d, J = 2.5 Hz, 1H), 7.33 (d, J = 8.0 Hz, 1H), 7.25 (t, J = 1.5 Hz, 1H), 6.91-6.89 (m, 1H), 5.27 (s, 2H), 4.66 (s, 2H), 3.80 (s, 3H) | 171.49 | 27.43 |
| 8-2 | CO₂H | H | CF₃ | 1H-NMR (500 MHz, CDCl3) δ 7.47 (s, 1H), 7.42 (d, J = 8.0 Hz, 1H), 7.35 (d, J = 6.5 Hz, 1H), 7.30 (t, J = 7.5 Hz, 1H), 6.92 (t, J = 15.5 Hz, 2H), 6.74 (s, 1H),6.57 (s, 1H), 5.01 (s, 2H), 4.17 (s, 2H) 1.86 (s, 3H). | 130.73 | N/A |
| 8-3 | CO₂CH₃ | OCH₃ | H | 1H-NMR (500 MHz, CDCl3) δ 7.36 (d, J = 6.5 Hz, 2H), 7.34-7.27 (m, 2H), 7.25 (d, J = 2.0 Hz, 1H), 6.91-6.89 (m, 3H), 5.16 (s, 2H), 4.67 (s, 2H), 3.81 (t, J = 2.0 Hz, 6H), 2.21 (s, 3H). | 151.78 | 6.32 |
| 8-4 | CO₂H | OCH₃ | H | 1H-NMR (500 MHz, CDCl3) δ 7.36 (d, J = 8.5 Hz, 2H), 7.29 (d, J = 7.5 Hz, 2H), 6.908-6.891 (m, 3H), 5.16 (s, 2H), 4.70 (s, 2H), 3.81 (s, 3H), 2.21 (d, J = 2.0 Hz, 3) | 182.06 | 9.88 |
| 8-5 | CO₂CH₃ | Br | H | 1H-NMR (500 MHz, CDCl3) δ 7.52-7.50 (m, 2H), 7.32-7.27 (m, 3H), 6.94-6.92 (m, 1H), 5.20 (s, 2H), 4.67 (s, 2H), 3.82 (s, 3H), 2.26 (s, 3H); 13C-NMR (CDCl3, 125 MHz) δ 169.2, 157.7, 154.7, 138.0, 137.1, 131.5, 129.8, 129.5, 121.7, 119.7, 115.3, 112.4, 75.4, 65.3, 52.3, 12.8; LRMS (ESI+) m/z 391.84 [M]+. | 149.13 | N/A (Tox.) |
| 8-6 | CO₂H | Br | H | 1H-NMR (500 MHz, CDCl3) δ 7.51-7.50 (t, 2H, J = 2 Hz), 7.34-7.27 (m, 3H), 6.95-6.93 (m, 1H), 5.20 (s, 2H), 4.73 (s, 1H), 2.27 (s, 3H); 13C-NMR (CDCl3, 125 MHz) δ 174.2, 157.4, 154.9, 138.0, 137.0, 131.5, 129.8, 129.6, 121.8, 120.0, 115.3, 112.4, 75.4, 64.8, 13.0; LRMS (ESI+) m/z 378.99 [M]+. | 123.78 | N/A (Tox.) |
| 8-7 | CO₂X, X = (2pyridyl) methylamine | Br | H | 1H-NMR (CDCl3, 500 MHz) δ 8.60-8.58 (m, 1H), 7.95 (s, 1H), 7.80 (s, 1H), 7.52-7.50 (d, J = 8.5 Hz, 2H), 7.46-7.44 (m, 1H), 7.35-7.27 (m, 5H), 7.01-6.98 (m, 1H), 5.20 (s, 2H), 4.76-4.75 (d, J = 5.5 Hz, 2H), 4.60 (s, 2H), 2.26 (s, 3H); 13C-NMR (CDCl3, 500 MHz) δ 168.46, 157.31, 155.52, 154.74, 148.40, 147.44, 138.77, 138.16, 137.08, 131.52, 129.85, 123.15, 121.76, 119.99, 115.66, 112.40, 75.45, 67.40, 43.18, 12.92; LRMS (ESI+) m/z 468.49 [M]+. | 129.69 | N/A |
| 8-8 | CO₂Y, Y = histamine | Br | H | 1H-NMR (CDCl3, 500 MHz) δ 8.95 (s, 1H), 7.51-7.46 (m, 2H), 7.29-7.22 (m, 4H), 7.03 (s, 1H), 6.89-6.88 (d, J = 6.5 Hz, 1H), 5.16 (s, 2H), 4.53 (s, 2H), 3.67 (s, 2H), 3.00 (s, 2H), 2.22 | 121.10 | N/A (Tox.) |

TABLE 1-continued

| Compound | R³ | R⁴ | R⁵ | Analysis data (1H/13C-NMR or LC-MS) | Max (%) | EC₅₀ |
|---|---|---|---|---|---|---|
| | | | | (s, 3H); 13C-NMR (CDCl3, 500 MHz) δ 157.1, 154.8, 137.0, 131.5, 130.9, 129.7, 121.7, 115.8, 115.3, 112.4, 75.3, 67.2, 24.9, 13.0; LRMS (ESI+) m/z 494.26 [M + Na]+. | | |
| 8-9 | CO₂CH₃ | NO₂ | H | 1H-NMR (500 MHz, CDCl3) δ 7.36 (d, J = 6.5 Hz, 2H), 7.34-7.27 (m, 2H), 7.25 (d, J = 2.0 Hz, 1H), 6.91-6.89 (m, 3H), 5.16 (s, 2H), 4.67 (s, 2H), 3.81 (t, J = 2.0 Hz, 6H), 2.21 (s, 3H) | 193.04 | 6.44 |
| 8-10 | CO₂H | NO₂ | H | 1H-NMR (500 MHz, CDCl3) δ 7.36 (d, J = 8.5 Hz, 2H), 7.29 (d, J = 7.5 Hz, 2H), 6.91-6.89 (m, 3H), 5.16 (s, 2H), 4.70 (s, 2H), 3.81 (s, 3H), 2.21 (s, 3H). | 161.26 | 10.17 |
| 8-11 | CO₂CH₃ | SO₂CH₃ | H | 1H-NMR (500 MHz, CDCl3) δ 7.93 (d, J = 8.5 Hz, 2H), 7.59 (d, J = 1.5 Hz, 2H), 7.30-7.25 (m 1H), 7.24-7.22 (m 2H), 6.91-6.89 (m 1H), 5.31 (s, 2H), 4.65 (s, 2H), 3.80 (s, 3H), 3.06 (s, 3H), 2.28 (s, 3H). | 104.72 | N/A |
| 8-12 | CO₂H | SO₂CH₃ | H | 1H-NMR (500 MHz, MeOH) δ 7.96 (d, J = 7.0 Hz, 2H), 7.67 (d, J = 8.5 Hz, 2H), 7.30-7.21 (m 3H), 6.96-6.94 (m 1H), 6.91-6.89 (m 1H), 5.32 (s, 2H), 4.67 (s, 2H), 3.11 (s, 3H), 2.27 (s, 3H). | 98.71 | N/A |
| 8-13 | CO₂CH₃ | F | H | 1H-NMR (500 MHz, CDCl3) δ 7.39-7.36 (m, 2H), 7.29 (s, 1H), 7.228 (t, J = 2.5 1H), 7.059-7.024 (m, 2H), 6.90-6.88 (m, 1H), 5.18 (s, 2H), 4.65 (s, 2H), 3.81 (s, 3H). | 119.93 | N/A (Tox.) |
| 8-14 | CO₂H | F | H | 1H-NMR (500 MHz, CDCl3) δ 7.38-7.36 (m, 2H), 7.35 (s, 1H), 7.23 (s, 1H), 7.03 (t, J = 8.5 2H), 6.90 (t, J = 3.0 1H), 5.17 (s, 2H), 4.66 (s, 2H), 2.20 (s, 3H). | N/D | N/D |

[Chemical Formula 9]

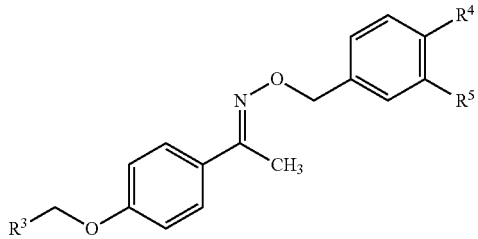

| 9-1 | CO₂CH₃ | H | CF₃ | 1H-NMR (500 MHz, CDCl3) δ 7.66 (s, 1H), 7.59-7.55 (m, 4H), 7.48 (d, J = 7.5 Hz, 1H), 6.89-6.87 (m, 2H) 5.25 (s, 2H), 4.65 (s, 2H), 3.80 (s, 3H), 2.25 (s, 3H). | 107.89 | N/A |
| 9-2 | CO₂H | H | CF₃ | 1H-NMR (500 MHz, CDCl3) δ 7.66 (s, 1H), 7.60-7.55 (m, 4H), 7.48 (d, J = 8.0 Hz, 2H), 6.91-6.89 (m, 2H), 5.26 (s, 2H), 4.70 (s, 2H), 2.26 (s, 3H). | 115.15 | N/A |
| 9-3 | CO₂CH₃ | OCH₃ | H | 1H-NMR (500 MHz, CDCl3) δ 7.60-7.59 (m, 2H), 7.36-7.35 (m, 2H), 6.90-6.88 (m, 4H), 5.14 (s, 2H), 4.65 (s, 2H), 3.81 (d, J = 2.5 Hz, 6H), 2.21 (s, 3H) | 103.87 | N/A |
| 9-4 | CO₂H | OCH₃ | H | 1H-NMR (500 MHz, CDCl3) δ 7.61 (d, J = 9.0 Hz, 2H), 7.35 (d, J = 8.5 Hz, 2H), 6.91-6.89 (m, 4H), 5.14 (s, 2H), 4.69 (s, 2H), 3.81 (s, 3H), 2.21 (s, 3H). | 102.65 | N/A |
| 9-5 | CO₂CH₃ | Br | H | 1H-NMR (500 MHz, CDCl3) δ 7.58-7.56 (d, 2H, J = 9 Hz), 7.48-7.47 (d, 2H, J = 8 Hz), 7.28-7.25 (d, 2H, J = 8.5 Hz), 6.89-6.87 (d, 2H, J = 9 Hz), 5.15 (s, 2H), 4.65 (s, 2H), 3.80 (s, | 111.88 | N/A |

TABLE 1-continued

| Compound | $R^3$ | $R^4$ | $R^5$ | Analysis data (1H/13C-NMR or LC-MS) | Max (%) | $EC_{50}$ |
|---|---|---|---|---|---|---|
| | | | | 3H), 2.22 (s, 3H); 13C-NMR (CDCl3, 125 MHz) δ 169.1, 158.5, 154.6, 137.3, 131.4, 130.1, 129.8, 127.5, 121.6, 114.4, 75.2, 65.2, 52.3, 12.8; LRMS (ESI+) m/z 392.13 [M]+. | | |
| 9-6 | $CO_2H$ | Br | H | 1H-NMR (500 MHz, CDCl3) δ 7.56-7.51 (m, 4H), 7.35-7.34 (d, 2H, J = 8.5), 5.12 (s, 2H), 4.39 (s, 2H), 2.16 (s, 3H); 13C-NMR (CDCl3, 125 MHz) δ 159.4, 154.3, 137.7, 131.2, 130.1, 127.8, 127.0, 120.7, 114.3, 74.2, 66.3, 12.4; LRMS (ESI+) m/z 400.78 [M + Na]+. | 106.70 | N/A |
| 9-7 | $CO_2X$, X = (2-pyridyl) methylamine | Br | H | 1H-NMR (MeOD, 500 MHz) δ 7.90 (s, 1H), 7.62-7.60 (d, 2H), 7.52-7.50 (d, 2H), 7.34 (s, 2H), 6.96-6.95 (d, J = 8.5 Hz, 3H), 5.16 (s, 2H), 4.52 (s, 2H), 3.56 (s, 2H), 2.86 (s, 2H), 2.24 (s, 3H); 13C-NMR (MeOD, 500 MHz) δ 169.56, 158.56, 154.76, 137.70, 134.38, 133.68, 131.07, 129.95, 129.58, 127.26, 121.09, 116.35, 114.25, 74.70, 66.79, 25.80, 11.44; LRMS (ESI+) m/z 493.06 [M + Na]+. | 135.47 | N/A |
| 9-8 | $CO_2Y$, Y = histamine | Br | H | 1H-NMR (CDCl3, 500 MHz) δ 8.74 (s, 1H), 8.62 (s, 1H), 8.31 (s, 1H), 7.96 (s, 1H), 7.75 (s, 1H), 7.53-7.48 (m, 4H), 7.26-7.25 (d, J = 1.0 Hz, 2H), 6.99-6.97 (d, J = 8.0 Hz, 2H), 5.14 (s, 1H), 4.97 (s, 1H), 4.52 (s, 1H), 2.21 (s, 1H); 13C-NMR (CDCl3, 500 MHz) δ 168.43, 158.03, 155.18, 154.57, 146.73, 139.55, 137.28, 131.48, 130.40, 129.81, 127.64, 123.74, 123.42, 121.67, 114.68, 75.26, 67.30, 42.81, 30.93, 12.80; LRMS (ESI+) m/z 490.00 [M + Na]+. | 120.89 | N/A |
| 9-9 | $CO_2CH_3$ | $NO_2$ | H | 1H-NMR (500 MHz, CDCl3) δ 8.22 (d, J = 9.0 Hz, 2H), 7.57-7.53 (m, 4H), 6.89 (d, J = 9.0 2H), 5.30 (s, 2H), 4.64 (s, 2H), 3.80 (s, 3H), 3.27 (s, 3H). | 113.52 | N/A |
| 9-10 | $CO_2H$ | $NO_2$ | H | 1H-NMR (500 MHz, CDCl3) δ 8.22 (d, J = 7.0 Hz, 2H), 7.59-7.54 (m, 4H), 6.90 (d, J = 7.5 2H), 5.30 (s, 2H), 4.69 (s, 2H), 2.28 (s, 3H). | 108.43 | N/A |
| 9-11 | $CO_2CH_3$ | $SO_2CH_3$ | H | 1H-NMR (500 MHz, CDCl3) δ 7.94 (d, J = 8.5 Hz, 2H), 7.59-7.56 (m, 4H), 6.89 (m 2H), 5.29 (s 2H), 4.65 (s, 2H), 3.80 (s, 3H), 3.05 (s, 3H), 2.27 (s, 3H). | 100.39 | N/A |
| 9-12 | $CO_2H$ | $SO_2CH_3$ | H | 1H-NMR (500 MHz, MeOH) δ 7.95 (d, J = 8.5 Hz, 2H), 7.65 (d, J = 8.5 Hz, 2H), 7.60 (d, J = 9.0 Hz, 2H), 6.93-6.91 (m, 2H), 5.29 (s 2H), 4.67 (s, 2H), 3.11 (s, 3H), 2.27 (s, 3H). | 111.38 | N/A |
| 9-13 | $CO_2CH_3$ | H | $CF_3$ | 1H-NMR (500 MHz, CDCl3) δ 7.66 (s, 1H), 7.59-7.55 (m, 4H), 7.48 (d, J = 7.5 Hz, 1H), 6.89-6.87 (m, 2H) 5.25 (s, 2H), 4.65 (s, 2H), 3.80 (s, 3H), 2.25 (s, 3H). | 107.89 | N/A |

Experimental Example 1. Evaluation of Efficacy on Transcriptional Activity of CLOCK:BMAL1 Dimer The NIH-3T3 fibroblast line (Non-patent document 6) expressing the E-box-LUC reporter was used to evaluate the effect of the oxyiminomethylbenzene derivative on the transcriptional activity of the CLOCK:BMAL1 dimer mediated by E-box. Reporter-expressing fibroblast line was maintained and cultured in an incubator in a humidified state at 5% carbon dioxide and 37 degrees Celsius, using Dulbecco's modified eagles medium (Invitrogen) having 10% fetal bovine serum, 1% penicillin/streptomycin (Invitrogen) and 1% L-glutamine added thereto.

The reporter-expressing cell line was dispensed and cultured in a 48-well culture plate 24 hours before compound treatment. The cultured cells were finally treated with a compound to a concentration of 0.1, 0.3, 1.0, 3.0, 10, 30 or 100 μM. As a control group (0 μM), cells treated with the same amount of dimethyl sulfoxide (DMSO) were used. After 36 hours elapsed after treatment of the compound, the cells were washed twice with 1× D-PBS, and was lysed for 15 minutes using 100 μl of a cell lysis buffer (Promega) per well. After reacting a 20 μl sample of the lysate with the same amount of a luciferase assay reagent (Promega), the luciferase activity was measured using a luminometer (TD-20/20 Luminometer, Turner systems). The measured luciferase activity was corrected based on the protein content of the lysate. The protein content was measured using a Bradford staining reagent from Bio-rad.

The concentration-response correlation for each derivative was converted to a standard curve using Four Parameter Logistic Equation. The calculation process utilized the statistical analysis function provided by SigmaPlot 10.0 (SigmaPlot 8.0, Systat Software Inc.). Based on the concentration-response curve, the maximum activity (Max) and $EC_{50}$ values of each derivative were calculated and input in [Table 1]. When the compound induces cell death, cytotoxicity (Tox.) was input to the $EC_{50}$ field. The concentration-reaction correlation curves of compounds of Chemical Formula 8-9, 9-9, 8-10 and 9-10 as a representative example are shown in FIG. 1.

As shown in FIG. 1 and Table 1, among the compounds of Example 1, the compound of Chemical Formula 8-9 has a maximum activity of 193.04% compared to the control group, and $EC_{50}$ value thereof was 6.44 μM. No significant cytotoxicity was observed at up to 100 μM thereof. Thus, the compound of Chemical Formula 8-9 was found to be the best in terms of maximal activity, $EC_{50}$ and cytotoxicity. The compound of Chemical Formula 8-10 which have a structure similar to Chemical Formula 8-9 also showed a significant level of maximal activity (161.26%) and $EC_{50}$ value (10.17 μM).

Experimental Example 2. Verification of CRY Dependency Via Compound Treatment

In order to verify whether the compounds (Chemical Formula 8-9 and 8-10) prepared in Example 1 actually regulate E-box-mediated transcriptional activity via CRY, the following experiment was performed.

The HEK293 cell line used in this experiment was maintained and cultured in Dulbecco's modified Eagle medium supplemented with 10% serum, 1% penicillin/streptomycin, and 1% L-glutamine in an incubator under a humidified state at 5% carbon dioxide and 37 degrees Celsius. After dispensing HEK293 cells into a 48-well culture plate 24 hours before transduction, a mouse CLOCK expression vector (600 ng/well) and mouse BMAL1 expression vector (200 ng/well) or the same amount of pcDNA3.1 plasmid and Flag-CRY1 expression vector (20 ng/well) or the same amount of pcDNA3.1 plasmid together with E-box-LUC luciferase reporter (50 ng/well), and pRL-mTK reporter (100 ng/well) were introduced into the cells. Lipofectamine (Lipofectamine 3000, Invitrogen) was used for transfection. The procedure was carried out according to the producer's manual.

After 48 hours from the transduction, a compound of Chemical Formula 9-9 or 8-10 was finally applied to become a concentration of 1, 3 or 10 μM. As a control group (0 μM), one treated with the same amount of dimethyl sulfoxide was used. After 36 hours elapsed after the application of the compound, the cells were washed twice with 1× D-PBS, and was lysed for 15 minutes with 100 μl of cell lysis buffer solution per well. After reacting a 20 μl sample of the lysate with the same amount of the luciferase activity evaluation reagent, the luciferase activity was measured using a luminometer. The measured activity of E-box-LUC luciferase was corrected using the activity of pRL-mTK ranilla luciferase introduced together therewith.

Figure 2:
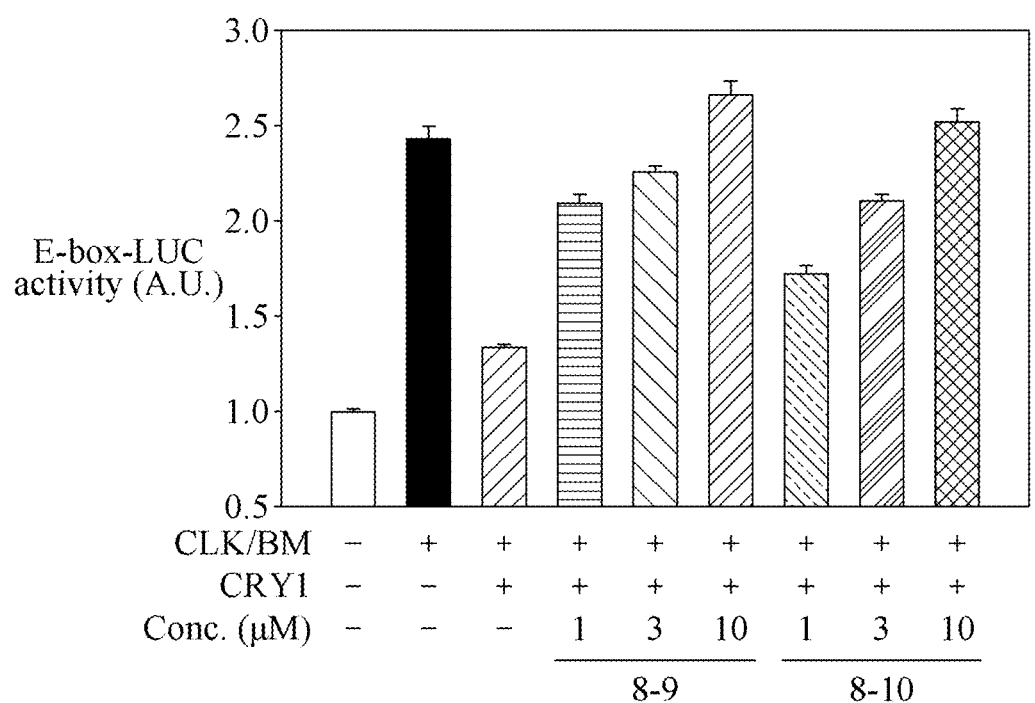
FIG. 2 shows a result that the increase in E-box-LUC reporter activity by CLOCK:BMAL1 dimer (C/B) is inhibited by overexpression of CRY1, and inhibition of CLOCK:BMAL1 activity by CRY1 is recovered in a concentration-dependent manner by treatment of compounds of Chemical Formula 8-9 and 8-10 among the oxyiminomethylbenzene derivatives.

The change in E-box-LUC reporter activity in each experimental group for each derivative treatment was converted into a ratio to the average value of the control (CTL, a group to which only E-box-LUC luciferase reporter, pRL-mTK reporter, and pcDNA3.1 were introduced, and which was treated with dimethyl sulfoxide) and was shown in [FIG. 2]. As a result, as is known, the expression of CRY1 inhibited the E-box-mediated transcriptional activity of CLOCK:BMAL1 at a significant level, and the action of CRY was inhibited in a concentration-dependent manner upon application of the compound of Chemical Formula 8-9 and 8-10.

As shown in FIG. 2, among the compounds of Example 1, the compounds of Chemical Formula 8-9 and 8-10 promote the transcriptional activity of CLOCK:BMAL1 in a CRY-dependent manner. Thus, the oxyiminomethylbenzene derivative in accordance with the present disclosure act as inhibitors for the CRY protein.

Experimental Example 3. Evaluation of Efficacy of Derivatives on Circadian Rhythm Expression of PER2-LUC Fusion Protein The effects of the compounds (8-9 and 8-10) prepared in Example 1 on the circadian rhythm expression of the molecular biological clock whose the cells are expressed through inhibition of CRY and enhancement of transcriptional activity of CLOCK:BMAL1 were evaluated. To this end, a mutant fibroblast line (PER2-LUC knock-in fibroblast) was used in which a PER2-LUC fusion protein is expressed via linking the luciferase gene from the position where the stop codon of the PER2 gene is located. The cell line was established from lung tissue of PER2-LUC knock-in mutant mice (Non-patent document 31) 1 week after birth. PER2-LUC knock-in (KI) fibroblasts was maintained and cultured in the incubator under a humidified state at 5% carbon dioxide and 37 degrees Celsius using Dulbecco's modified Eagle medium supplemented with 10% serum, 1% penicillin/streptomycin, and 1% L-glutamine.

PER2-LUC KI cells were dispensed into a 35 mm culture dish 24 hours and cultured before compound treatment. After treating the cultured cells with 200 nM dexamethasone (DEX) for 2 hours for synchronization, the DEX was replaced with a medium including the substrate of luciferase that is, luciferin (final concentration 0.1 mM) with 20 μM of the compound of Chemical Formula 8-9 or 8-10. As a control group, cells (VEH) treated with the same amount of dimethyl sulfoxide instead of the compound were used. As another comparative group, the cells treated with a 2-ethoxypropionic acid-based CRY inhibitor (Non-patent document 6), that is, KS15 (final concentration 20 μM) was used. The control and the KS15-treated cells were also replaced with a medium including luciferin of the same concentration.

Bioluminescence signals generated from cells cultured in a medium including the compound and luciferin were continuously measured for up to 5 days at 10-minute intervals using a real-time bioluminescence measurement equipment (Kronos-DIO, ATTO). The results were identified through statistical detrending. The circadian rhythm expression pattern of the PER2-LUC fusion protein was analyzed using the Cosinor analysis program (free distribution on http://www.circadian.org) to determine the amplitude, period, and robustness of the periodicity. Based on the results obtained through 4 replicate experiments, the statistical significance of the change according to compound treatment was verified.

Figure 3A:
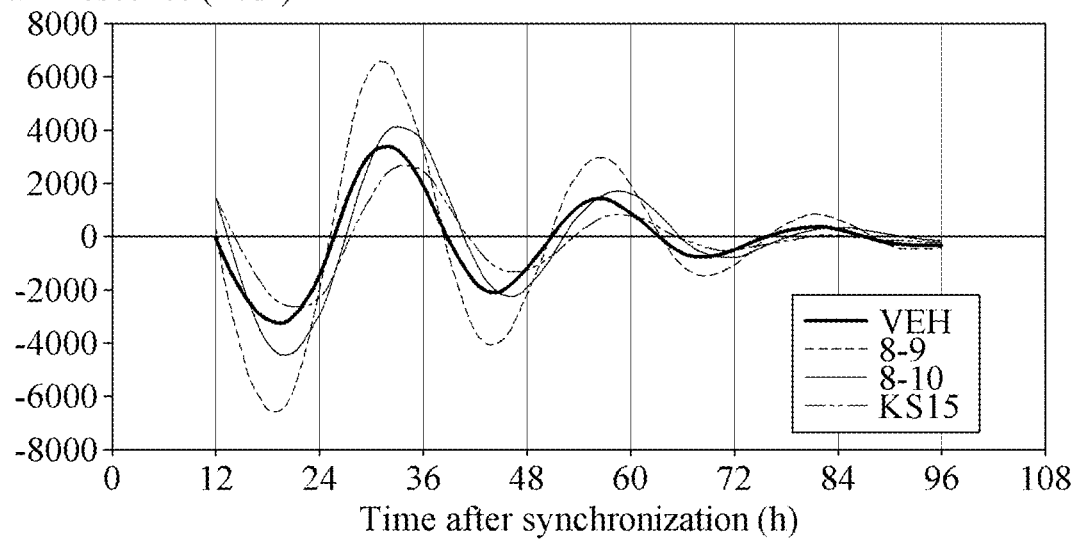
FIGS. 3A and 3B show the result of evaluation of the effect of compounds of Chemical Formula 8-9 and 8-10 among the oxyiminomethylbenzene derivatives on the circadian rhythmicity of the molecular clock as measured by cyclic accumulation of PER2-LUC fusion protein observed in fibroblast cultures, which have been established from PER2-LUC knock-in mice, as compared to KS15 as a CRY inhibitor based on 2-ethoxypropionic acid derivatives.
Figure 3B:
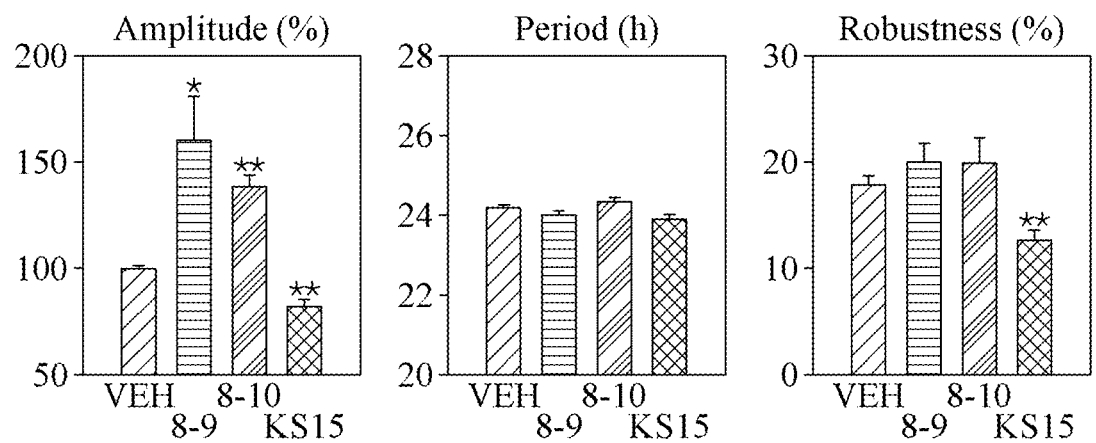

As a result, as shown in FIGS. 3A and 3B, treatment of compound of Chemical Formula 8-9 or 8-10 increases the amplitude of the circadian rhythm expression of the PER2-LUC fusion protein at a significant level, while not affecting the period or robustness. This is in stark contrast to KS15, in which the treatment of KS15 enhances the transcriptional activity of the CLOCK:BMAL1 dimer, but decreases the amplitude of the circadian rhythm molecular rhythm, and reduces the robustness by a significant level. In other words, unlike 2-ethoxypropionic acid derivatives such as KS15, the oxyiminomethylbenzene derivative in accordance with the present disclosure have an enhancing effect on the circadian molecular rhythm exhibited by individual cells.

Further, the oxyiminomethylbenzene derivative represented by Chemical Formula 1 according to the present disclosure may be formulated in various forms depending on purposes. The following exemplifies several formulation methods in which the compound represented by Chemical Formula 1 is contained as an active ingredient according to the present disclosure.

Formulation Example 1. Preparation of Tablets (Pressurized Method)

As an active ingredient, 5.0 mg of Compound represented by Chemical Formula 1 of the present disclosure was sieved, and was mixed with 14.1 mg of lactose, 0.8 mg of crospovidone USNF, and 0.1 mg of magnesium stearate and then the mixture was pressed into a tablet.

Formulation Example 2. Preparation of Tablets (Wet Granulation)

As an active ingredient, 5.0 mg of Compound represented by Chemical Formula 1 of the present disclosure was sieved, and then was mixed with 16.0 mg of lactose and 4.0 mg of starch. After dissolving 0.3 mg of polysorbate 80 in pure water, an appropriate amount of this solution was added to the mixture, followed by atomization. After drying, the fine particles were sieved and mixed with 2.7 mg of colloidal silicon dioxide and 2.0 mg of magnesium stearate. The fine particles were pressed into tablets.

Formulation Example 3. Preparation of Powder and Capsule

As an active ingredient, 5.0 mg of Compound represented by Chemical Formula 1 of the present disclosure was sieved, and then mixed with 14.8 mg of lactose, 10.0 mg of polyvinyl pyrrolidone, and 0.2 mg of magnesium stearate. The mixture is filled into solid No. 5 gelatin capsules using a suitable device.

Formulation Example 4. Preparation of Injection

As an active ingredient, 100 mg of Compound represented by Chemical Formula 1 of the present disclosure was mixed with 180 mg of mannitol, 26 mg of Na2HPO4, 12H2O, and 2,974 mg of distilled water to prepare the injection.

Although the example embodiments have been described based on the limited drawings as described above, a person of ordinary skill in the art may apply various technical modifications and variations thereto. For example, even when the described steps are performed in a different order from that in the described method, and/or the described components are combined with each other in a manner different from that as described above, or are replaced or substituted with other components or equivalents, appropriate results may be achieved.

Therefore, other implementations, other example embodiments, and equivalents to claims fall within the scope of the following claims.

The invention claimed is:

1. A pharmaceutical composition comprising an oxyiminomethylbenzene derivative or a pharmaceutically acceptable salt thereof, wherein the oxyiminomethylbenzene derivative is a compound selected from a group consisting of:

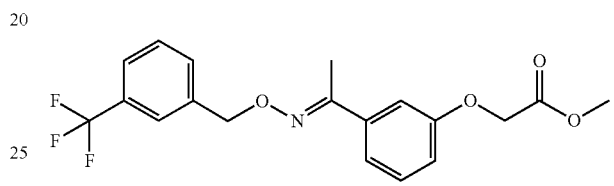

methyl 2-{3-[N-{[3-(trifluoromethyl)phenyl] methoxy}ethanimidoyl]phenoxy}acetate;

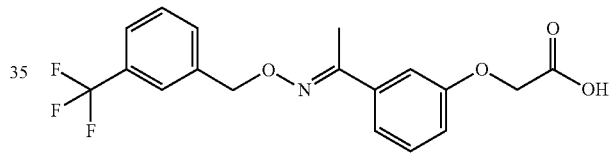

{3-[N-{[3-(trifluoromethyl)phenyl] methoxy}ethanimidoyl]phenoxy}acetic acid;

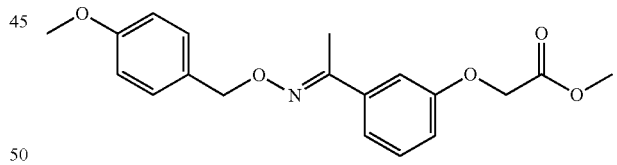

methyl 2-(3-{N-[(4-methoxyphenyl)methoxy] ethanimidoyl}phenoxy)acetate;

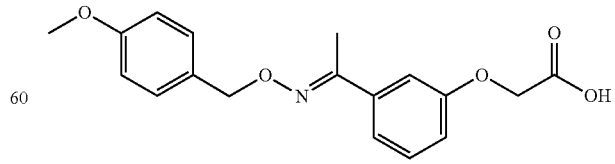

(3-{N-[(4-methoxyphenyl)methoxy] ethanimidoyl}phenoxy)acetic acid;

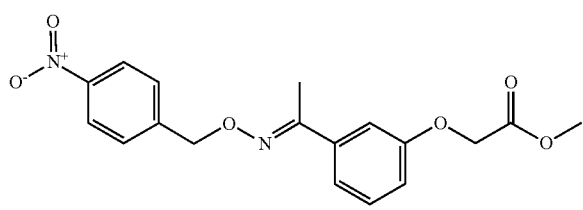 [SMILES: COC(=O)COc1cccc(/C(C)=N/OCc2ccc([N+](=O)[O-])cc2)c1]

methyl 2-(3-{N-[(4-nitrophenyl)methoxy]ethanimidoyl}phenoxy)acetate; and

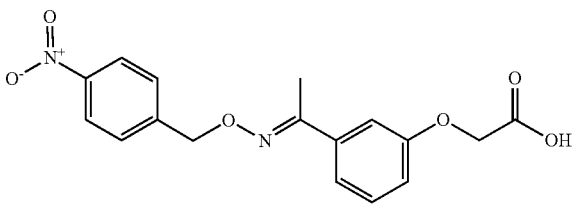 [SMILES: C/C(=N\OCc1ccc([N+](=O)[O-])cc1)c1cccc(OCC(=O)O)c1]

(3-{N-[(4-nitrophenyl)methoxy]ethanimidoyl}phenoxy)acetic acid.

2. A method for preventing or treating circadian rhythm-related diseases in an individual, comprising administering to the individual a pharmaceutical composition according to claim 1, wherein the circadian rhythm-related diseases are prevented or treated in the individual.

3. The method of claim 2, wherein the circadian rhythm-related disease comprises sleep disorder, metabolic disorder, cardiovascular disease, immune and inflammatory disease, mood disorder, addiction disorder, degenerative brain disease or cancer.

4. The method of claim 3, wherein the sleep disorder comprises jet lag syndrome, shift work sleep disorder, progressive sleep phase syndrome, sleep phase delay syndrome, respiratory related sleep disorder, restless legs syndrome, or REM sleep behavior disorder.

5. The method of claim 3, wherein the metabolic disorder comprises obesity, hypertension, hyperlipidemia, hyperglycemia, or polyuria.

6. The method of claim 3, wherein the mood disorder comprises depression, bipolar mood disorder, seasonal disorder, or anxiety disorder.

7. The method of claim 3, wherein the degenerative brain disease comprises Alzheimer's disease, Parkinson's disease, Huntington's disease, or dementia disease.

8. The method of claim 3, wherein the cardiovascular disease comprises ischemic heart disease, acute myocardial infarction, cerebral infarction, or atrial fibrillation.

9. The method of claim 3, wherein the cancer comprises colon cancer, stomach cancer, prostate cancer, breast cancer, kidney cancer, liver cancer, lung cancer, uterine cancer, colon cancer, pancreatic cancer, ovarian cancer, blood cancer, or brain tumor.

10. The pharmaceutical composition of claim 1, wherein the oxyiminomethylbenzene derivative enhances an amplitude of a circadian rhythm and stabilizes the rhythmicity thereof by inhibiting feedback actions of CRYs as a transcriptional regulator of a circadian molecular clockwork, and by enhancing activity of CLOCK:BMAL1 dimer.

* * * * *